(12) United States Patent
Kwon et al.

(10) Patent No.: US 12,421,491 B2
(45) Date of Patent: Sep. 23, 2025

(54) COMPOSITION FOR INCREASING BIOLOGICAL ACTIVITY OF STEM CELLS USING MIXTURE 4F

(71) Applicant: YOUTH BIO GLOBAL CO., LTD., Seoul (KR)

(72) Inventors: Sang Mo Kwon, Guri-si (KR); Yeon Ju Kim, Gumi-si (KR)

(73) Assignee: YOUTH BIO GLOBAL CO., LTD., Seoul (KR)

( * ) Notice: Subject to any disclaimer, the term of this patent is extended or adjusted under 35 U.S.C. 154(b) by 932 days.

(21) Appl. No.: 17/461,209

(22) Filed: Aug. 30, 2021

(65) Prior Publication Data

US 2021/0395674 A1    Dec. 23, 2021

Related U.S. Application Data

(63) Continuation of application No. PCT/KR2020/009037, filed on Jul. 9, 2020.

(30) Foreign Application Priority Data

Jul. 9, 2019    (KR) .................... 10-2019-0082712

(51) Int. Cl.
| | | |
|---|---|---|
| C12N 5/00 | (2006.01) | |
| A61K 31/575 | (2006.01) | |
| A61K 31/7048 | (2006.01) | |
| A61K 31/737 | (2006.01) | |
| A61K 38/18 | (2006.01) | |
| A61P 9/10 | (2006.01) | |

(52) U.S. Cl.
CPC .......... C12N 5/0056 (2013.01); A61K 31/575 (2013.01); A61K 31/7048 (2013.01); A61K 31/737 (2013.01); A61K 38/1866 (2013.01); A61P 9/10 (2018.01)

(58) Field of Classification Search
CPC combination set(s) only.
See application file for complete search history.

(56) References Cited

FOREIGN PATENT DOCUMENTS

| KR | 10-2011-0024660 A | 3/2011 |
|---|---|---|
| KR | 10-1555941 B1 | 9/2015 |
| KR | 10-1555945 B1 | 9/2015 |
| KR | 10-2088767 B1 | 3/2020 |

OTHER PUBLICATIONS

Lee JH, Lee SH, Choi SH, Asahara T, Kwon SM. The sulfated polysaccharide fucoidan rescues senescence of endothelial colony-forming cells for ischemic repair. Stem Cells. Jun. 2015;33(6):1939-51. doi: 10.1002/stem.1973. PMID: 25693733. (Year: 2015).*

Koyama S, Sato E, Tsukadaira A, Haniuda M, Numanami H, Kurai M, Nagai S, Izumi T. Vascular endothelial growth factor mRNA and protein expression in airway epithelial cell lines in vitro. Eur Respir J. Dec. 2002;20(6):1449-56. doi: 10.1183/09031936.02.00089802. PMID: 12503703. (Year: 2002).*

Bauman E, Granja PL, Barrias CC. Fetal bovine serum-free culture of endothelial progenitor cells-progress and challenges. J Tissue Eng Regen Med. Jul. 2018;12(7):1567-1578. doi: 10.1002/term.2678. Epub May 30, 2018. PMID: 29701896. (Year: 2018).*

Moon SH, Kim SM, Park SJ, Kim H, Bae D, Choi YS, Chung HM. Development of a xeno-free autologous culture system for endothelial progenitor cells derived from human umbilical cord blood. PLoS One. Sep. 24, 2013;8(9):e75224. doi: 10.1371/journal.pone.0075224. PMID: 24086472; PMCID: PMC3782462. (Year: 2013).*

International Search Report issued in PCT/KR2020/009037; mailed Oct. 16, 2020.

Kim, Y.-J. et al. "Long-Term Priming by Three Small Molecules Is a Promising Strategy for Enhancing Late Endothelial Progenitor Cell Bioactivities." Molecules and Cells; Jun. 12, 2018; vol. 41, No. 6; pp. 582-590.

Li, L. et al. "VEGF promotes endothelial progenitor cell differentiation and vascular repair through connexin 43." Stem Cell Research & Therapy; Oct. 24, 2017; vol. 8, No. 237; pp. 1-11.

* cited by examiner

*Primary Examiner* — Fereydoun G Sajjadi
*Assistant Examiner* — Qinhua Gu
(74) *Attorney, Agent, or Firm* — Studebaker Brackett PLLC

(57) ABSTRACT

The present disclosure relates to a composition for increasing the biological activity of stem cells using mixture 4F. Stem cells treated with mixture 4F according to the present disclosure not only acquire undifferentiated characteristics (stemness), but also have the advantage of improving cell proliferative ability and mobility, and thus, after being transplanted into a body, the stem cells can improve cell survival and engraftment and further enhance the ability to regenerate blood vessels and tissues. Accordingly, the stem cells can have various applications in the fields of stem cell differentiation and ischemic disease prevention or treatment.

6 Claims, 36 Drawing Sheets

Specification includes a Sequence Listing.

FIG. 6B

Analysis of vascular endothelial cell undifferentiation/differentiation-related gene expression

| Name | FPKM_1 | FPKM_2 | log$_2$(FPKM_2/FPKM_1) | p-value | q-value |
|---|---|---|---|---|---|
| CD34 | 110.372 | 480.499 | 2.12216 | 5.00E-05 | 0.0050058 |
| KIT | 4.77294 | 15.5911 | 1.70778 | 5.00E-05 | 0.0050058 |
| CXCR4 | 40.3378 | 496.744 | 3.6223 | 5.00E-05 | 0.0050058 |
| FLT4 | 11.0386 | 41.4908 | 1.91022 | 5.00E-05 | 0.0050058 |
| IL3RA | 9.79643 | 36.7644 | 1.90798 | 5.00E-05 | 0.0050058 |
| HEY1 | 6.05122 | 39.5059 | 2.70691 | 5.00E-05 | 0.0050058 |
| CXCR7 | 13.1274 | 123.367 | 3.2323 | 5.00E-05 | 0.0050058 |
| NOTCH4 | 15.9593 | 56.2289 | 1.81692 | 5.00E-05 | 0.0050058 |
| HLX | 11.3457 | 61.9857 | 2.44979 | 5.00E-05 | 0.0050058 |
| RARg | 8.70353 | 39.4359 | 2.17984 | 5.00E-05 | 0.0050058 |
| ZFP36 | 3.5965 | 14.0594 | 1.96687 | 0.00015 | 0.0124694 |
| NR4BP | 29.2675 | 85.4954 | 1.54651 | 5.00E-05 | 0.0050058 |
| RCAN1 | 13.1031 | 35.4785 | 1.43704 | 0.0001 | 0.0089989 |
| EFNA1 | 38.5096 | 102.285 | 1.4093 | 0.00015 | 0.0124694 |
| PODXL | 84.4 | 255 | 1.59 | 0.0004 | 0.0086076 |
| VWA1 | 1.64 | 22.6 | 3.78 | 5.00E-05 | 0.005006 |
| UNC5B | 1.92 | 74.2 | 5.27 | 5.00E-05 | 0.005006 |
| PLVAP | 6 | 228 | 5.25 | 5.00E-05 | 0.005006 |
| ESM1 | 89.9 | 926 | 3.36 | 5.00E-05 | 0.005006 |
| ANGPT2 | 7.58 | 62.4 | 3.04 | 5.00E-05 | 0.005006 |
| CDH5 | 370 | 429 | 0.216 | 0.612 | 0.999975 |
| MCAM | 816 | 2.24E+03 | 1.46 | 0.027 | 0.465041 |
| TIE1 | 457 | 455 | -0.00532 | 0.9935 | 0.999975 |
| SELE | 0.0081 | 1.09 | 3.59 | 0.0659 | 0.999975 |
| VCAM1 | 0.0258 | 2.03 | 6.34 | 0.00345 | 0.999975 |
| KDR | 188 | 229 | 0.283 | 0.53575 | 0.999975 |
| KLF2 | 9.84 | 9.85 | 0.00229 | 0.9983 | 0.999975 |
| FOXO1 | 20.3 | 28.1 | 0.388 | 0.4825 | 0.999975 |
| ETV2 | 0.829 | 1.01 | 0.277 | 0.7769 | 0.999975 |
| GATA6 | 4.4 | 3.11 | -0.798 | 0.17855 | 0.999975 |

FIG. 17A

Analysis of vascular endothelial cell undifferentiation/differentiation-related gene expression

| Name | FPKM_1 | FPKM_2 | log₂(FPKM_2/FPKM_1) | p-value | q-value |
|---|---|---|---|---|---|
| CD34 | 110.372 | 480.499 | 2.12216 | 5.00E-05 | 0.0050058 |
| KIT | 4.77224 | 15.5911 | 1.70770 | 5.00E-05 | 0.0050058 |
| CXCR4 | 40.3379 | 496.744 | 3.6223 | 5.00E-05 | 0.0050058 |
| FLT4 | 11.0386 | 41.4906 | 1.91022 | 5.00E-05 | 0.0050058 |
| IL3RA | 9.79843 | 36.7644 | 1.90798 | 5.00E-05 | 0.0050058 |
| HEY1 | 6.05122 | 39.5069 | 2.70681 | 5.00E-05 | 0.0050058 |
| CXCR7 | 13.1274 | 123.367 | 3.2323 | 5.00E-05 | 0.0050058 |
| NOTCH4 | 15.9593 | 56.2289 | 1.81692 | 5.00E-05 | 0.0050058 |
| HLX | 11.2457 | 61.9857 | 2.44979 | 5.00E-05 | 0.0050058 |
| RARg | 8.70353 | 39.4359 | 2.17984 | 5.00E-05 | 0.0050058 |
| ZFP36 | 3.5965 | 14.0594 | 1.96687 | 0.00015 | 0.0124984 |
| NRARP | 29.2675 | 85.4904 | 1.54661 | 5.00E-05 | 0.0050058 |
| RCAN1 | 13.1031 | 35.4708 | 1.43704 | 0.00001 | 0.0093059 |
| EFNA1 | 33.6096 | 102.285 | 1.4693 | 0.00015 | 0.0124984 |
| PODXL | 84.4 | 255 | 1.59 | 0.00004 | 0.026076 |
| VWA1 | 1.64 | 22.6 | 3.78 | 5.00E-05 | 0.005006 |
| UNC5B | 1.92 | 74.2 | 5.27 | 5.00E-05 | 0.005006 |
| PLVAP | 6 | 228 | 5.25 | 5.00E-05 | 0.005006 |
| ESM1 | 89.9 | 926 | 3.36 | 5.00E-05 | 0.005006 |
| ANGPT2 | 7.58 | 62.4 | 3.04 | 5.00E-05 | 0.005006 |
| CDH5 | 370 | 429 | 0.216 | 0.632 | 0.99975 |
| MCAM | 816 | 2.24E+03 | 1.46 | 0.027 | 0.466041 |
| TIE1 | 457 | 455 | -0.00632 | 0.99155 | 0.99975 |
| SELE | 0.0681 | 1.05 | 3.59 | 0.0059 | 0.18595 |
| VCAM1 | 0.0256 | 2.08 | 6.34 | 0.00545 | 0.176194 |
| KDR | 198 | 229 | 0.283 | 0.53575 | 0.99975 |
| KLF2 | 9.84 | 9.85 | 0.00229 | 0.9983 | 0.99975 |
| FOXO1 | 30.3 | 23.1 | -0.388 | 0.4835 | 0.99975 |
| ETV2 | 0.829 | 1.01 | 0.277 | 0.7769 | 0.99975 |
| GATA6 | 5.4 | 3.11 | -0.798 | 0.12855 | 0.99975 |

SEQUENCE LISTING

<160> NUMBER OF SEQ ID NOS: 10

<210> SEQ ID NO 1
<211> LENGTH: 20
<212> TYPE: DNA

```
<213> ORGANISM: Artificial Sequence
<220> FEATURE:
<223> OTHER INFORMATION: VEGF-A_Forward

<400> SEQUENCE: 1
gctcggtgct ggaatttgat                                          20

<210> SEQ ID NO 2
<211> LENGTH: 20
<212> TYPE: DNA
<213> ORGANISM: Artificial Sequence
<220> FEATURE:
<223> OTHER INFORMATION: VEGF-A_Reverse

<400> SEQUENCE: 2
gcccgattca agtggggaat                                          20

<210> SEQ ID NO 3
<211> LENGTH: 22
<212> TYPE: DNA
<213> ORGANISM: Artificial Sequence
<220> FEATURE:
<223> OTHER INFORMATION: IL-8_Forward

<400> SEQUENCE: 3
caccggaagg aaccatctca ct                                       22

<210> SEQ ID NO 4
<211> LENGTH: 24
<212> TYPE: DNA
<213> ORGANISM: Artificial Sequence
<220> FEATURE:
<223> OTHER INFORMATION: IL-8_Reverse

<400> SEQUENCE: 4
tcagccctct tcaaaaactt ctcc                                     24

<210> SEQ ID NO 5
<211> LENGTH: 25
<212> TYPE: DNA
<213> ORGANISM: Artificial Sequence
<220> FEATURE:
<223> OTHER INFORMATION: b-FGF_Forward

<400> SEQUENCE: 5
ggagaagagc gaccctcaca tcaag                                    25

<210> SEQ ID NO 6
<211> LENGTH: 27
<212> TYPE: DNA
<213> ORGANISM: Artificial Sequence
<220> FEATURE:
<223> OTHER INFORMATION: b-FGF_Reverse

<400> SEQUENCE: 6
ccagttcgtt tcagtgccac ataccaa                                  27

<210> SEQ ID NO 7
<211> LENGTH: 20
<212> TYPE: DNA
<213> ORGANISM: Artificial Sequence
<220> FEATURE:
<223> OTHER INFORMATION: Ang2_Forward

<400> SEQUENCE: 7
gggaagggaa tgaggcttac                                          20
```

```
<210> SEQ ID NO 8
<211> LENGTH: 20
<212> TYPE: DNA
<213> ORGANISM: Artificial Sequence
<220> FEATURE:
<223> OTHER INFORMATION: Ang2_Reverse

<400> SEQUENCE: 8
aagttggaag gaccacatgc                                              20

<210> SEQ ID NO 9
<211> LENGTH: 20
<212> TYPE: DNA
<213> ORGANISM: Artificial Sequence
<220> FEATURE:
<223> OTHER INFORMATION: b-actin_Forward

<400> SEQUENCE: 9
agcgagcatc ccccaaagtt                                              20

<210> SEQ ID NO 10
<211> LENGTH: 20
<212> TYPE: DNA
<213> ORGANISM: Artificial Sequence
<220> FEATURE:
<223> OTHER INFORMATION: b-actin_Reverse

<400> SEQUENCE: 10
gggcacgaag gctcatcatt                                              20
```

COMPOSITION FOR INCREASING BIOLOGICAL ACTIVITY OF STEM CELLS USING MIXTURE 4F

CROSS-REFERENCE TO RELATED APPLICATION

The present application is a continuation of International Patent Application No. PCT/KR2020/009037, filed on Jul. 9, 2020, which is based upon and claims the benefit of priority to Korean Patent Application No. 10-2019-0082712 filed on Jul. 9, 2019. The disclosures of the above-listed applications are hereby incorporated by reference herein in their entirety.

BACKGROUND

1. Technical Field

The present disclosure relates to a composition for increasing the biological activity of stem cells using mixture 4F.

2. Description of Related Art

Ischemic vascular disease, such as heart disease, cerebrovascular disease, and peripheral vascular disease, has a high prevalence of 40% and is one of the diseases with the highest mortality rate worldwide. Existing main treatment methods therefor include three of a medical treatment centered on drug administration, a mechanical interventional treatment for blood vessels, and a surgical bypass surgery treatment. Even after all these treatments, there are not a few cases where satisfactory treatment is not possible due to the limited regeneration of ischemic tissue in which the smooth supply of oxygen and nutrients has not occurred. Accordingly, in the case of a wide range of vascular diseases that cannot be treated with current medical technology, angiogenesis therapy to secure blood flow to the ischemic tissue and reduce tissue damage by promoting angiogenesis from the tissue around the ischemic site as an alternative treatment has been proposed.

For the formation of vascular tissue composed of cells, it is necessary to supply the cells that make blood vessels. Accordingly, as a therapeutic strategy, many methods for promoting the proliferation and development of vascular endothelial cells by administering angiogenesis promoters directly or their genes are in progress. However, its effect is insignificant, and several side effects and safety issues have been raised, so more research is needed before its actual introduction.

Vascular endothelial progenitor cells have been found to be effective in repairing damaged blood vessels and regenerating ischemic tissue. From the discovery to the present, various studies have been attempted to promote angiogenesis by directly administering the cells that make blood vessels. Currently, in the field of angiogenesis and regeneration using stem cells, adult stem cells are used for clinical application. There are advantages in that they can be extracted from the patient's own body and auto-transplanted into the necessary tissue, and there is no ethical issue compared to embryonic stem cells. However, it is difficult to reach the commercialization stage due to the senescence and functional deterioration of patient-derived cells due to a westernized diet, reduced exercise, and senescence. Therefore, research for stem cell amplification and bioactivity enhancement is a key factor for the practical use of cell therapy. To this end, it is necessary to discover functional enhancing factors that are safe for the human body and to analyze the mechanism of action of each factor to have a system that can supply functionally superior stem cells. In response to this demand, recently, research on cell function enhancement for the practical application of stem cell therapeutics is being actively conducted. Research using gene introduction is a method of improving cell function through amplification and deletion of specific genes, and additional research on its stability is required.

SUMMARY

Accordingly, the present inventors have completed the present disclosure by developing mixture 4F containing fucoidan, a tauroursodeoxycholic acid, oleuropein, and a vascular endothelial growth factor in order to address an issue associated with some related art.

Accordingly, an aspect of the present disclosure is directed to providing a composition for inhibiting senescence, promoting proliferation or inducing differentiation of stem cells containing fucoidan, a tauroursodeoxycholic acid, oleuropein, and a vascular endothelial growth factor as active ingredients.

Another aspect of the present disclosure is directed to providing a pharmaceutical composition for preventing or treating an ischemic disease, wherein the pharmaceutical composition contains fucoidan, a tauroursodeoxycholic acid, oleuropein, and a vascular endothelial growth factor as active ingredients.

Still another aspect of the present disclosure is directed to providing a stem cell culture medium composition containing fucoidan, a tauroursodeoxycholic acid, oleuropein, and a vascular endothelial growth factor as active ingredients.

Still another aspect of the present disclosure is directed to providing a xeno-free culture method including treating stem cells with a stem cell culture medium composition containing fucoidan, a tauroursodeoxycholic acid, oleuropein, and a vascular endothelial growth factor as active ingredients.

Still another aspect of the present disclosure is directed to providing a stem cell treatment adjuvant containing fucoidan, a tauroursodeoxycholic acid, oleuropein, and a vascular endothelial growth factor as active ingredients.

Still another aspect of the present disclosure is directed to providing stem cells cultured through the xeno-free culture method.

Still another aspect of the present disclosure is directed to providing a pharmaceutical composition for preventing or treating an ischemic disease, wherein the pharmaceutical composition contains the stem cells.

To this end, the present disclosure provides a composition for inhibiting senescence, promoting proliferation or inducing differentiation of stem cells containing fucoidan, a tauroursodeoxycholic acid, oleuropein, and a vascular endothelial growth factor as active ingredients.

The present disclosure provides a pharmaceutical composition for preventing or treating ischemic disease, wherein the pharmaceutical composition contains fucoidan, a tauroursodeoxycholic acid, oleuropein, and a vascular endothelial growth factor as active ingredients.

The present disclosure provides a stem cell culture medium composition containing fucoidan, a tauroursodeoxycholic acid, oleuropein, and a vascular endothelial growth factor as active ingredients.

The present disclosure provides a xeno-free culture method including treating stem cells with a stem cell culture medium composition containing fucoidan, a touroursodeoxycholic acid, oleuropein, and a vascular endothelial growth factor as active ingredients.

The present disclosure provides a stem cell treatment adjuvant containing fucoidan, a touroursodeoxycholic acid, oleuropein, and a vascular endothelial growth factor as active ingredients.

The present disclosure provides stem cells cultured through the xeno-free culture method.

The present disclosure provides a pharmaceutical composition for preventing or treating an ischemic disease, wherein the pharmaceutical composition contains the stem cells.

The stem cells treated with mixture 4F according to the present disclosure not only acquire undifferentiated characteristics (sternness), but also have the advantage of improving cell proliferative ability and mobility, thereby improving cell survival and engraftment after transplantation of stem cells into the body and further enhancing the ability to regenerate blood vessels and tissues. Accordingly, the stem cells treated with mixture 4F can have various applications in the fields of stem cell differentiation and ischemic disease prevention and treatment.

BRIEF DESCRIPTION OF THE DRAWINGS

FIG. 6B is a diagram illustrating a result of analyzing the gene expression of the undifferentiated stem cell-related marker according to the treatment with mixture 4F of the present disclosure as a main component analysis and a heat map.

FIG. 17A is a diagram illustrating a result of analyzing the gene expression levels of vascular stem cells and control cells cultured by the xeno-free culture method using mixture 4F according to the present disclosure.

DETAILED DESCRIPTION

Figure 1:
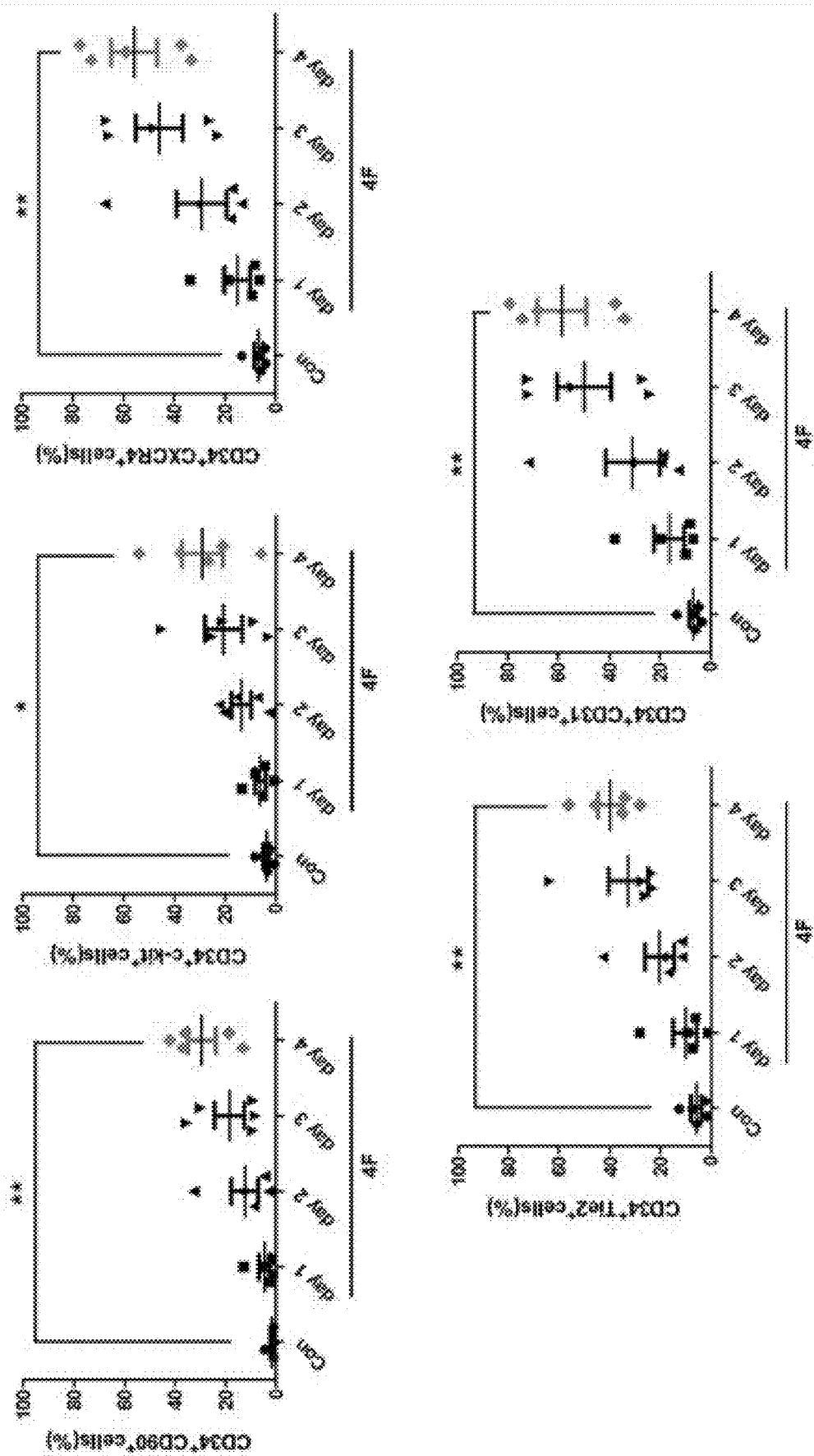
FIG. 1 is a diagram illustrating a result of identifying the effect of mixture 4F according to the present disclosure on the phenotype of cells.

Hereinafter, the present disclosure will be described in detail.

According to an aspect of the present disclosure, the present disclosure provides a composition for inhibiting senescence, promoting proliferation or inducing differentiation of stem cells containing fucoidan, a tauroursodeoxycholic acid, oleuropein, and a vascular endothelial growth factor as active ingredients.

In the present disclosure, mixture 4F means a mixture of fucoidan, a tauroursodeoxycholic acid, oleuropein, and a vascular endothelial growth factor.

In the present disclosure, the term "stem cells" refer to cells capable of differentiating into at least two types of cells while having self-replicating capability, and may be classified as totipotent stem cells, pluripotent stem cells, and multipotent stem cells. The stem cells of the present disclosure may be selected properly without any limitation according to purposes, and be derived from adult cells of all the known tissue or cells obtained from mammals, for example, from bone marrow, umbilical cord blood, placenta (or placental tissue cells), or adipose tissue (adipose tissue cells). For example, the stem cells may be obtained without any limitation from bone marrow, adipose tissue, muscular tissue, ex vivo cultured autologous mesenchymal stem cells, allogenic mesenchymal stem cells, umbilical cord blood, embryonicyolk sac, placenta, umbilical cord, periosteum, skin from fetuses and adolescence, and blood. The stem cells may be derived from fetuses, newborns, or adults.

According to a specific embodiment of the present disclosure, the stem cells may be selected from the group consisting of endothelial progenitor cells, angiogenic stem cells, mesenchymal stem cells, embryonic stem cells, myoblasts, and cardiac stem cells, preferably be endothelial progenitor cells or angiogenic stem cells, and most preferably endothelial progenitor cells.

In the present disclosure, the term "senescence" refers to a halt or significant delay in cell growth and cell division against diverse internal or external stress (e.g., high concentration of oxygen in continuous passages and in vitro culture), from which stem cells suffer.

In the present disclosure, the term "proliferation" in refers to increase in the number of a characteristic cell type, or cell types, from an initial cell population of cells, which may or may not be identical. The initial cells used for proliferation may not be the same as the cells generated from proliferation.

In the present disclosure, the term "differentiation induction" includes not only complete differentiation induction of stem cells into specific cells, but also formation of embryonic bodies formed in an intermediate stage before complete differentiation of stem cells into specific cells.

According to a specific embodiment of the present disclosure, the differentiation may be angiogenesis.

In the present disclosure, the term "angiogenesis" refers to a process through which new blood vessels are formed, i.e., new blood vessels being generated and differentiated into cells, tissue, or organs.

In the present disclosure, angiogenesis includes vascular regeneration, vascular repair, and vascular differentiation, which are involved in the formation of new blood vessels, in addition to activation, migration, and proliferation of endothelial cells, reformation of matrix, and stabilization of cells.

In order to repair ischemic tissue caused by vascular damage, the formation of new blood vessels is necessary. The proliferation of preexisting vascular endothelial cells alone is insufficient for angiogenesis and repair. Thus, it is significant in the angiogenesis process to mobilize angiogenic stem cells derived from bone marrow to an ischemic site to be involved in vascular recovery.

According to the present disclosure, the composition promotes mobilization of angiogenic stem cells from bone marrow to ischemic tissue, increases integration capability with vascular endothelial cells, and increases differentiation potential into blood vessels.

In the present disclosure, fucoidan is a polysaccharide in which fucose, which is a basic sugar, and a sulfate group are combined, and is contained in large amounts in brown algae. The fucoidan is known to have an anticoagulant action, an antitumor action, a gastric ulcer treatment promoting action, an antibacterial action, an inhibitory action on blood pressure increase, an induction of hepatocellular growth factor (HGF) production, an inhibitory action on blood sugar rise, an immune cell regulation action, an anti-allergic action, and an antiviral action.

In a specific embodiment of the present disclosure, fucoidan is preferably represented by the following Formula 1, but is not limited thereto.

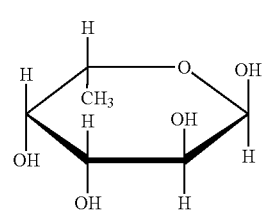

[Formula 1]

In a specific embodiment of the present disclosure, the composition according to the present disclosure contains fucoidan at a concentration of 1 to 300 nM, more preferably 50 to 250 nM, and most preferably 150 nM.

In the present disclosure, the term "tauroursodeoxycholic acid (TUDCA)" refers to a taurine conjugate of a ursodeoxycholic acid (UDCA), and is known to be useful for the treatment of gallstones, liver cirrhosis, Huntington's disease, Parkinson's disease and stroke.

In a specific embodiment of the present disclosure, a tauroursodeoxycholic acid is preferably represented by the following Formula 2, but is not limited thereto.

[Formula 2]

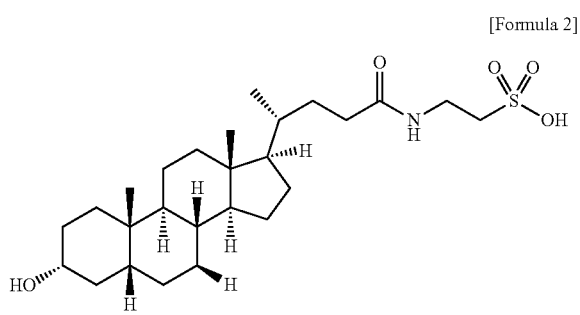

In a specific embodiment of the present disclosure, the composition according to the present disclosure contains a tauroursodeoxycholic acid at a concentration of 2.5 to 250 μM, preferably 12.5 to 50 μM, more preferably 17.5 to 35 μM, and most preferably 25 μM.

In the present disclosure, the term "oleuropein" refers to polyphenols present in olive fruits and olive leaves.

In a specific embodiment of the present disclosure, oleuropein is preferably represented by the following Formula 3, but is not limited thereto.

[Formula 3]

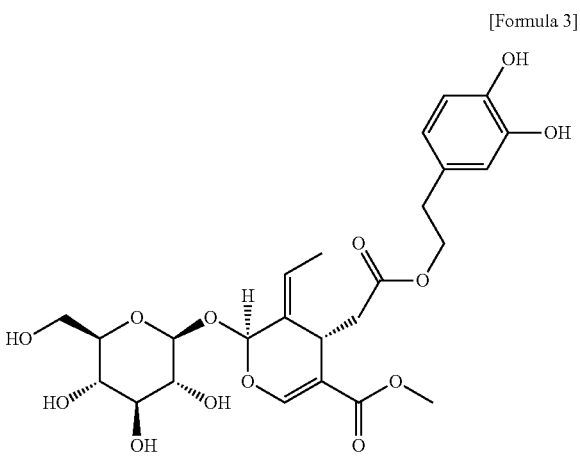 [SMILES: C/C=C1/[C@H](O[C@@H]2O[C@H](CO)[C@@H](O)[C@H](O)[C@H]2O)OC=C(C(=O)OC)[C@H]1CC(=O)OCCc1ccc(O)c(O)c1]

In a specific embodiment of the present disclosure, the composition according to the present disclosure contains oleuropein at a concentration of 0.05 to 5 μM, preferably 0.25 to 1 μM, more preferably 0.35 to 0.7 μM, and most preferably 0.5 μM.

In the present disclosure, the vascular endothelial growth factor (VEGF) is a signal protein produced by cells that stimulates vasculogenesis. The vascular endothelial growth factor is involved in vasculogenesis and angiogenesis.

In a specific embodiment of the present disclosure, the vascular endothelial growth factor is preferably at least one selected from the group consisting of VEGF-A, VEGF-B, VEGF-C and PlGF, but is not limited thereto.

In a specific embodiment of the present disclosure, the composition according to the present disclosure contains the vascular endothelial growth factor at a concentration of 0.1 to 10 nM, preferably 1 to 5 nM, and most preferably of 2.5 nM.

According to another aspect of the present disclosure, the present disclosure provides a pharmaceutical composition for preventing or treating an ischemic disease, wherein the pharmaceutical composition contains fucoidan, a tauroursodeoxycholic acid, oleuropein, and a vascular endothelial growth factor as active ingredients.

In addition, the present disclosure provides a method for preventing or treating an ischemic disease, wherein the method includes treating a subject with the pharmaceutical composition.

In addition, the present disclosure provides a use of the pharmaceutical composition for preventing or treating an ischemic disease.

In the present disclosure, the term "ischemic disease" refers to a disease caused by a decrease in blood supply to a body organ, tissue or site caused by constriction or occlusion of blood vessels. After ischemia of the tissue or site, even when reperfusion of blood occurs, nerve cells are damaged, causing various sequelae, and ultimately leads to irreversible damage, that is, necrosis of cells and tissues. The ischemic disease may be selected from the group consisting of ischemic heart disease, ischemic myocardial infarction, ischemic heart failure, ischemic gastroenteritis, ischemic vascular disease, ischemic ocular disease, ischemic retinopathy, ischemic glaucoma, ischemic kidney failure, ischemic boldness, ischemic stroke, and ischemic limb disease, more preferably selected from the group consisting of ischemic heart disease, ischemic myocardial infarction, ischemic heart failure, ischemic gastroenteritis, ischemic vascular disease, ischemic stroke, and ischemic limb disease, and most preferably ischemic stroke, and ischemic hindlimb disease.

In still another aspect of the present disclosure, the present disclosure provides a stem cell culture medium composition containing fucoidan, a tauroursodeoxycholic acid, oleuropein, and a vascular endothelial growth factor as active ingredients.

In the present disclosure, the term "culture media" means media which assure the growth and survival of stem cells in vitro, and which may include all of the pertinent media typically used in the art. The culture media and conditions depend on the kind of stem cells. Preferable is a cell culture minimum medium (CCMM), which generally comprises a carbon source, a nitrogen source and trace elements. Examples of the CCMM include, but are not limited to, DMEM (Dulbecco's Modified Eagle's Medium), MEM (Minimal essential Medium), BME (Basal Medium Eagle), RPMI1640, F-10, F-12, aMEM (a Minimal essential Medium), GMEM (Glasgow's Minimal essential Medium), and Iscove's Modified Dulbecco's Medium.

In a specific embodiment of the present disclosure, the medium composition of the present disclosure is preferably a xeno-free medium excluding cytokines or growth factors and animal serum (FBS) added to the existing culture medium, but is not limited thereto.

In addition, the present disclosure provides a xeno-free culture method including treating stem cells with a stem cell culture medium composition containing fucoidan, a tauroursodeoxycholic acid, oleuropein, and a vascular endothelial growth factor as active ingredients.

In still another aspect of the present disclosure, the present disclosure provides stem cells cultured by the culture method.

In a specific embodiment of the present disclosure, the stem cells may be selected from the group consisting of endothelial progenitor cells, angiogenic stem cells, mesenchymal stem cells, embryonic stem cells, myoblasts, and cardiac stem cells, preferably be endothelial progenitor cells or angiogenic stem cells, and most preferably endothelial progenitor cells.

The stem cells cultured by the xeno-free culture method according to the present disclosure not only acquire undifferentiated characteristics (stemness), but also have the advantage of improving angiogenesis, cell proliferative ability and mobility, thereby improving cell survival and engraftment after transplantation of vascular endothelial progenitor cells into the body and further enhancing the ability to regenerate blood vessels and tissues.

In this regard, in still another aspect of the present disclosure, the present disclosure provides a pharmaceutical composition for preventing or treating an ischemic disease, wherein the pharmaceutical composition contains the stem cells.

In addition, the present disclosure provides a method for preventing or treating an ischemic disease, wherein the method includes treating a subject with the stem cells.

In addition, the present disclosure provides a use of the stem cells for preventing or treating an ischemic disease.

In the present disclosure, the term "subject" refers to a target in need of treatment of a disease, and more specifically, a human, or a mammal such as a non-human primate, a mouse, a rat, a dog, a cat, a horse or a cow.

The pharmaceutical composition of the present disclosure may be formulated and used in various forms according to conventional methods. For example, the pharmaceutical composition |[L1] may be formulated in oral formulations such as powders, granules, tablets, capsules, suspensions, emulsions, and syrups, and may be formulated and used in the form of external preparations, suppositories, and sterile injection solutions.

The composition of the present disclosure may contain at least one known active ingredient having a preventive or therapeutic effect on an ischemic disease together with the active ingredient.

The composition of the present disclosure may further comprise a pharmaceutically acceptable additive, and examples of the pharmaceutically acceptable additive may comprise starch, gelatinized starch, microcrystalline cellulose, lactose, povidone, colloidal silicon dioxide, calcium hydrogen phosphate, lactose, mannitol, taffy, Arabic gum, pregelatinized starch, corn starch, powdery cellulose, hydroxypropylcellulose, Opadry, sodium starch glycolate, Carnauba wax, synthetic aluminum silicate, stearic acid, magnesium stearate, aluminum stearate, calcium stearate, and saccharose. The pharmaceutically acceptable additive according to the present disclosure may preferably be included at 0.1 to 90 parts by weight with respect to the composition, but the present disclosure is not limited thereto.

The composition of the present disclosure may be administered in various oral and parenteral forms in actual clinical administration, and in preparation, may be formulated with typically used diluting agents or excipients such as a filler, a thickening agent, a binder, a wetting agent, a dispersant, and a surfactant. It is preferable to use those disclosed in Lamington's literature as suitable preparations known in the pertinent technical field.

Examples of a solid preparation for oral administration may include a tablet, a pill, powder, a granule, and a capsule, and such a solid preparation may be formulated by mixing at least one excipient, for example, starch, calcium carbonate, sucrose, lactose or gelatin. Also, rather than a simple excipient, lubricants such as magnesium stearate talc may be used. In addition, a liquid preparation for oral administration may be a suspension, a liquid for internal use, an emulsion and a syrup, and contain various excipients, for example, a wetting agent, a sweetener, a flavoring agent, and a preservative, in addition to a frequently used simple diluent such as water or liquid paraffin.

Examples of a preparation for parenteral administration may include a sterilized aqueous solution, a non-aqueous solvent, a suspension, an emulsion, a lyophilizing agent, and a suppository. As a non-aqueous solvent or suspension agent, propylene glycol, polyethylene glycol, a vegetable oil such as olive oil, or an injectable ester such as ethylolate may be used. As the base of a suppository, Witepsol, Macrogol, Tween 61, cacao butter, laurin fat or glycerogelatin may be used.

The fucoidan, tauroursodeoxycholic acid, oleuropein, and vascular endothelial growth factor of the present disclosure may be used in the form of pharmaceutically acceptable salts, and all salts, hydrates and solvates prepared by conventional methods are included.

The salt may be preferably an acid addition salt formed by a pharmaceutically acceptable free acid. The acid addition salt may be prepared using a conventional method. For example, the acid addition salt may be prepared by dissolving the compound in an excess of an aqueous acid solution and precipitating the salt using a water-miscible organic solvent such as methanol, ethanol, acetone or acetonitrile. Alternatively, the acid addition salt may be prepared by heating an equimolar amount of the compound and acid or alcohol (e.g., glycol monomethylether) in water, and then drying the mixture by evaporation or filtering the precipitated salt by suction. Free acids that may be used in the present disclosure may include organic acids and inorganic acids. Examples of the inorganic acids may include, but are not limited to, hydrochloric acid, phosphoric acid, sulfuric acid, nitric acid and the like, and examples of the organic acids may include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like.

In addition, a pharmaceutically acceptable metal salt may be prepared using a base. An alkali metal salt or an alkaline earth metal salt may be obtained, for example, by dissolving the compound in an excess of an alkali metal hydroxide or alkaline earth metal hydroxide solution, filtering the undissolved compound salt and evaporating and drying the filtrate. For use in pharmaceutics, it is particularly preferable to prepare a sodium, potassium or calcium salt, but the scope of the present disclosure is not limited thereto. In addition, a silver salt corresponding thereto may be obtained by reacting an alkali metal or alkaline earth metal salt with a suitable silver salt (e.g., silver nitrate).

Unless indicated otherwise, pharmaceutically acceptable salts of the compounds include salts of acidic or basic groups which may be present in the compounds. For example, pharmaceutically acceptable salts include sodium, calcium and potassium salts, etc. of hydroxyl group, and other pharmaceutically acceptable salts of amino group include hydrobromide, sulfate salt, hydrogen sulfate salt, phosphate salt, hydrogen phosphate salt, dihydrogen phosphate salt, acetate salt, succinate salt, citrate salt, tartrate salt, lactate salt, mandelate salt, methanesulfonate (mesylate) salt and p-toluenesulfonate (tosylate) salt, etc. Such salts |[L2] may be prepared by a salt preparation method known in the pertinent field.

The dosage of the pharmaceutical composition of the present disclosure may vary depending on formulation methods, administration methods, dosing intervals and/or administration routes of the pharmaceutical composition. Furthermore, it may vary depending on many factors including the type and extent of reaction to achieve by administration of the pharmaceutical composition, the type, age, weight, general health conditions, symptoms or severity of diseases, gender, diet, excretion of target subjects to be administered, and ingredients of other medical composition used together synchronously or asynchronously for the corresponding subject, and analogous factors well known in the medical field. Those having ordinary skill in the pertinent technical field can easily determine and prescribe the effective dosage for the intended treatment.

An administration route and administration method of the pharmaceutical composition of the present disclosure may each be independent, and are not particularly limited. Also, as long as the pharmaceutical composition can be delivered to a target site, it may be administered by any administration route and administration method.

The pharmaceutical composition may be administered orally or parenterally. The method for parenteral administration includes, for example, intravenous administration, intraperitoneal administration, intramuscular administration, transdermal administration, subcutaneous administration or the like.

The pharmaceutical composition of the present disclosure is used alone or in combination with surgery, radiotherapy, hormone treatment, chemotherapy, and methods using a biological response modifier for the prevention or treatment of an ischemic disease.

In still another aspect of the present disclosure, the present disclosure provides a stem cell treatment adjuvant containing fucoidan, a tauroursodeoxycholic acid, oleuropein, and a vascular endothelial growth factor as active ingredients.

In the present disclosure, the term "cell therapeutic agent" refers to a pharmaceutical used for treating, diagnosing, or preventing diseases through a series of actions including changing biological properties of cells by proliferating or selecting living autologous, allogenic, or xenogenic cells in vitro or using other ways, in order to restore functions of cells and tissue. Particularly, the stem cell therapeutic agent may be classified as an embryonic stem cell therapeutic agent and adult stem cell therapeutic agent.

In the present disclosure, the term "stem cell treatment adjuvant" refers to a preparation that can be used adjunctively for enhancing the effect of a stem cell therapeutic agent generally used in the pertinent field. By using the composition of the present disclosure, it is possible to promote differentiation and inhibit senescence of stem cells in a stem cell therapeutic agent, thereby increasing the effect of a therapeutic agent. In a preferred embodiment of the present disclosure, the stem cell treatment is ischemic disease treatment.

The stem cell treatment adjuvant may be administered to the human body through any general route as long as it can reach the target tissue.

The method for parenteral administration includes, for example, intraperitoneal administration, intravenous administration, intramuscular administration, and subcutaneous administration, but is not limited thereto.

The stem cell treatment adjuvant may also be administered using any device which can deliver an active ingredient to a target cell. The stem cell treatment adjuvant may be administered with a pharmaceutical carrier which is generally used for stem cell therapy. Examples of the carrier may include physiological saline solutions.

Hereinafter, the present disclosure will be described in more detail through examples. These examples are only for illustrating the present disclosure, and it will be apparent to those skilled in the art that the scope of the present disclosure is not to be construed as being limited by these examples.

EXAMPLES

Example 1. Preparation of Mixture 4F

Mixture 4F was prepared by mixing fucoidan (150 nM), a tauroursodeoxycholic acid (25 µM), oleuropein (0.5 µM) and a vascular endothelial growth factor (2.5 nM) (recombinant human VEGF 165). In the Examples to be described later, b-FGF, IGF, EGF, and an ascorbic acid added to the existing culture medium (EndoGo XF media, Bological Industries) were not used, but only 4F was added to the basal medium and used for the experiment.

Example 2. Identification of Morphological Characteristics of Vascular Endothelial Progenitor Cells by the Treatment with Mixture 4F In order to check the effect of F treatment on cell phenotype, major cell markers were largely divided into undifferentiated markers (stem cell markers) and endothelial lineage markers and analyzed using flow cytometry. Specifically, mixture 4F (Fucoidan, TUDCA, Oleuropein, VEGF) was added to umbilical cord blood-derived vascular endothelial progenitor cells (L-EPC) with 5% FBS and 1% penicillin/streptomycin to a basal medium for culturing vascular endothelial cells (EBM2, Lonza). After treatment with various period conditions, the expression of undifferentiated markers (CD34, CD90, c-kit, CXCR4) and endothelial cell linage markers (Tie2, CD31) was analyzed using flow cytometry. To verify the reproducibility of the results, L-EPC was isolated and cultured (n=5) from umbilical cord blood derived from 5 mothers to identify the expression of each marker. The results of identifying the morphological characteristics of vascular endothelial progenitor cells according to the treatment with mixture 4F are shown in FIG. 1.

As shown in FIG. 1, it was identified that the cell group expressing the undifferentiated marker and the cell group expressing the distinct differentiation marker of the endothelial cell linage while having an undifferentiated character were significantly increased in a number of days dependent on the treatment of 4F mixture. Thus, it was identified that the treatment with mixture 4F maintains the cultural characteristics of the endothelial cell linage of the original cells and at the same time increases only the undifferentiated characteristics (stemness), so that it has a phenotype and function similar to that of endothelial cells, and that as a higher step, the characteristics of vascular stem cells, which are known to have unipotency into endothelial cells, were further acquired.

Example 3. Identification of Cell Mobility According to the Treatment with Mixture 4F As it was identified that the expression of CXCR4, which is known to regulate the mobility of stem cells in a number of days dependent on the treatment of 4F mixture, the cell mobility, which is an essential process for angiogenesis and regeneration, was analyzed using SDF-1α, a ligand of CXCR4. Specifically, a transwell migration assay was performed to analyze cell mobility by chemokine stimulation. An 8.0 µm mesh membrane insert seeded with cells of each experimental group ($5\times10^4$ cells) was inserted into a culture plate, and SDF-1α (100 ng/ml), a chemokine that stimulates cell migration, was added to the bottom and then cultured. After 6 hours, the cells that had escaped the pores of the mesh membrane by SDF-1α stimulation at the bottom were stained with crystal violet to count the migrated cells. SDF-1α is a major cytokine secreted from ischemic tissue and recruiting cells involved in vascular and tissue regeneration. The results of identifying the cell mobility according to the treatment with mixture 4F are shown in FIG. 2.

Figure 2:
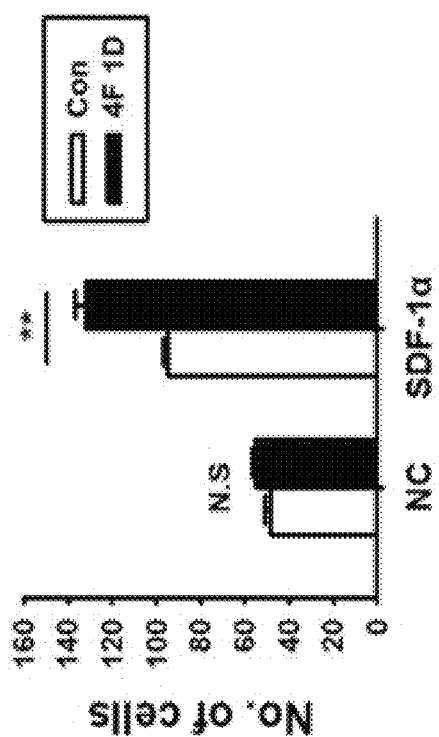
FIG. 2 is a diagram illustrating a result of identifying the cell mobility according to the treatment with mixture 4F according to the present disclosure.
Figure 2:
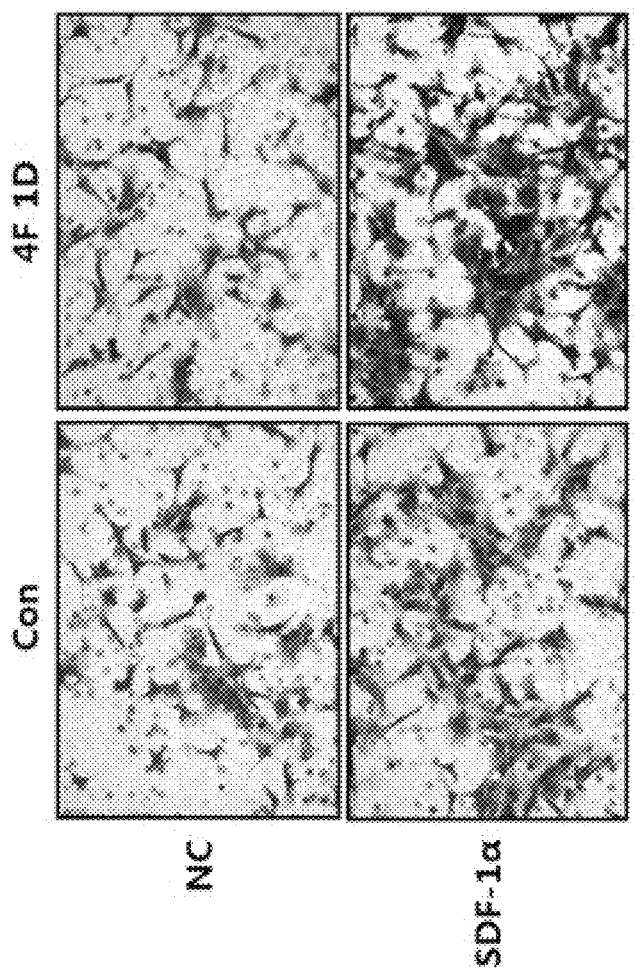

As shown in FIG. 2, the mobility of cells was significantly increased compared to the control by priming mixture 4F. In addition, it was identified that, although the level of mobility similar to that of the positive control group was observed in the negative control group, which was performed without specific stimulation, the cell mobility by SDF-1α stimulation according to the treatment with mixture 4F increased more than 3 times. These results indicate that priming of mixture 4F enhances the reactivity of cells to SDF-1α and the specific mobility to ischemic tissues.

Example 4. Identification of Vascular Regeneration Effect of Mixture 4F According to the Present Disclosure in an Animal Model of Lower Extremity Ischemia An animal model of lower extremity ischemia, a severe vascular disease model, was prepared and the therapeutic efficacy of vascular stem cells with enhanced function by treatment with mixture 4F was evaluated. Specifically, the degree of improvement in blood flow after cell transplantation was analyzed hemodynamically using a laser Doppler velocimeter. Specifically, to identify the therapeutic efficacy of cells primed with mixture 4F in a severe ischemic animal model, an animal model of lower extremity ischemia was prepared using 7-8 week old nude mice. The animal model of lower extremity ischemia is made by blocking blood flow to the lower extremities by femoral artery ligation. After blood vessel resection, cells ($5\times10^5$ cells/PBS 50 µl) were intramuscularly injected and the degree of recovery of blocked blood flow on a daily basis (3, 7, 14 days) was analyzed hemodynamically using a laser Doppler velocimeter. In addition, the engraftment, survival, and angiogenesis effects of the transplanted cells were identified through histological analysis through live cell imaging, and the results are shown in FIGS. 3A and 3B.

Figure 3A:
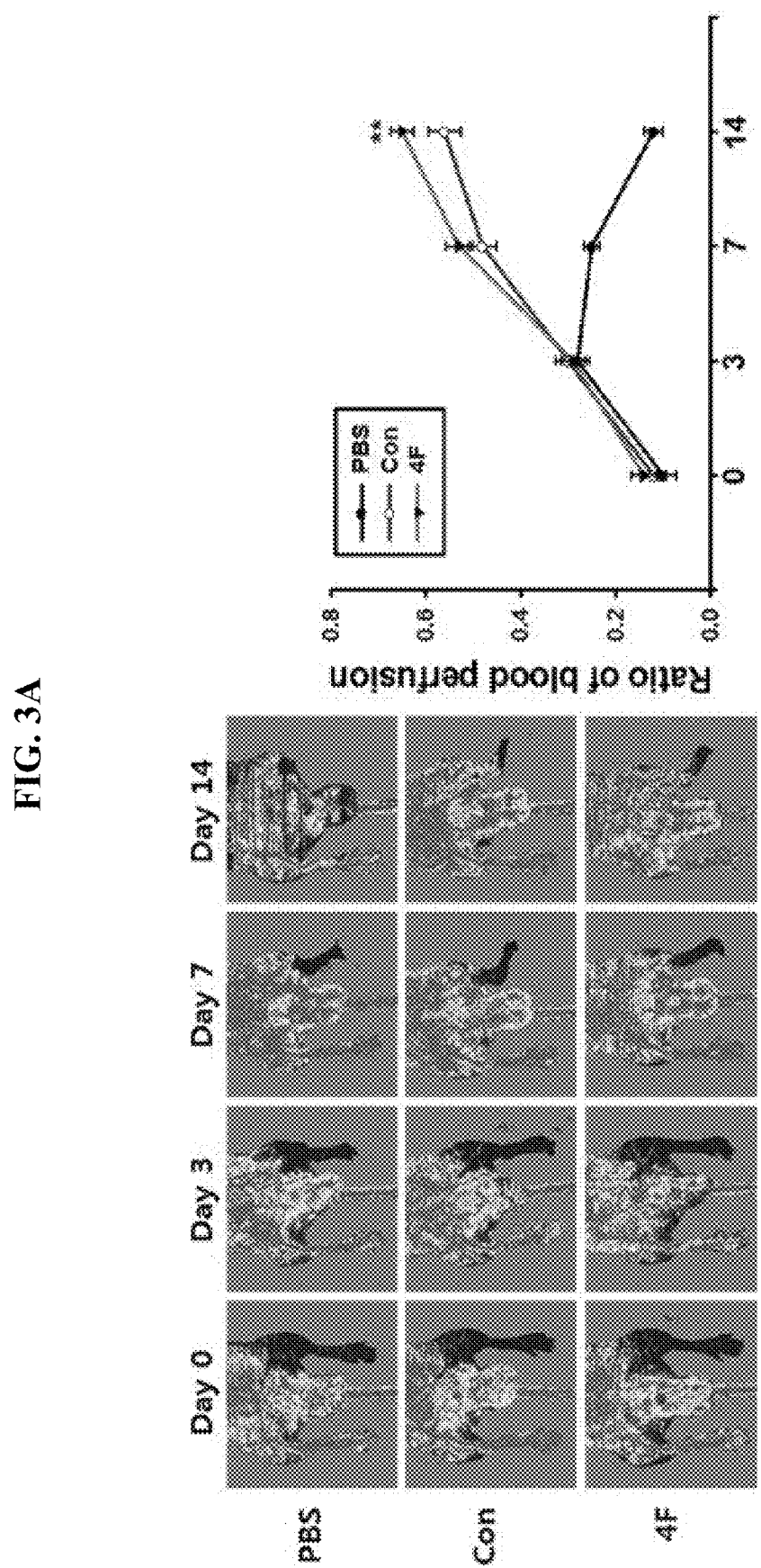
FIG. 3A is a diagram illustrating a result of identifying the effect of vascular regeneration in vivo after transplanting cells treated with mixture 4F according to the present disclosure in an animal model of lower extremity ischemia.

As shown in FIG. 3A, it was identified that, during transplantation of 4F-treated cells, the regeneration of blood vessels in vivo was significantly improved compared to the control group.

Figure 3B:
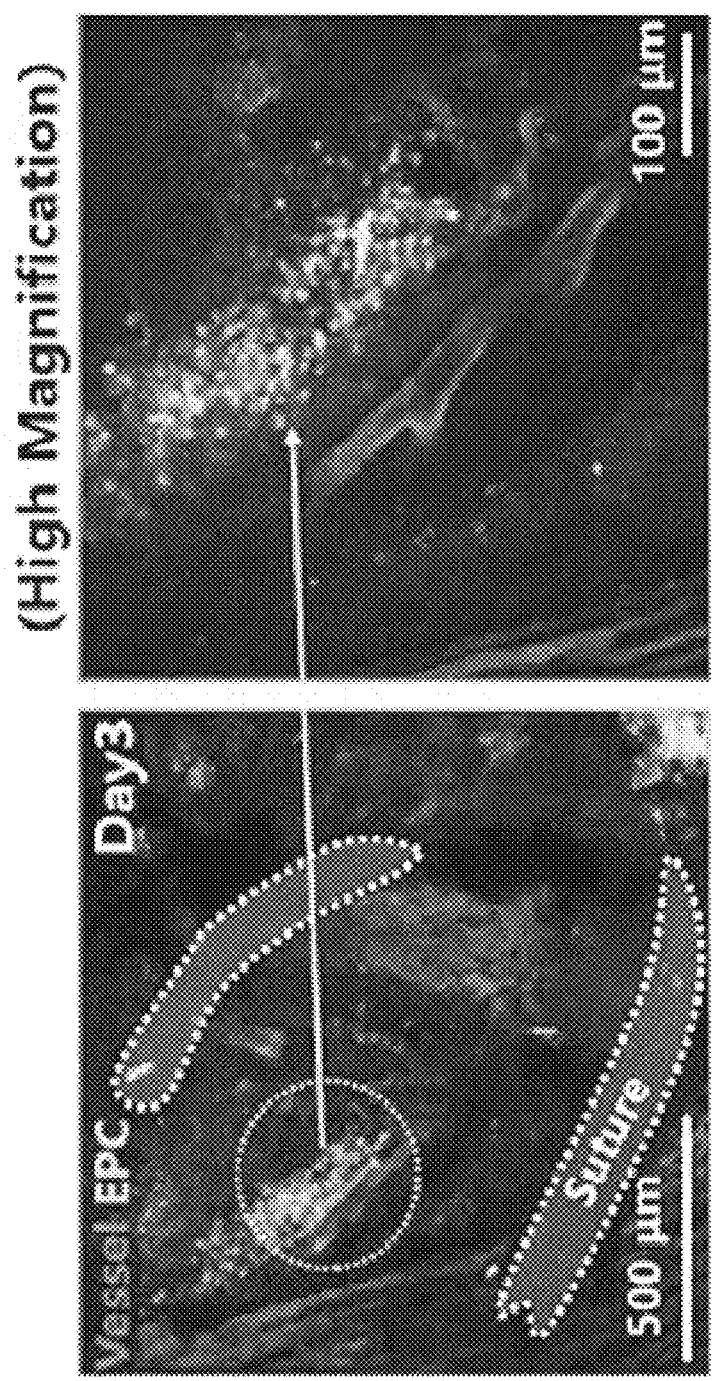
FIG. 3B is a diagram illustrating an image of a vascular suture site on day 3 after transplanting GFP-tagged cells using an in vivo imaging technique.
Figure 3B:

As shown in FIG. 3B, as a result of imaging the vascular suture site in a live state on the third day after transplantation of GFP-tagged cells using in vivo imaging technique, it was observed that a large number of $GFP^+$ cells transplanted around the sutured arterial vessel were observed. observed. The above result indicate that the vascular stem cells whose viability is enhanced by the treatment with mixture 4F were recruited for vascular regeneration.

Example 5. Identification of Cardiac Function Enhancement Effect According to the Treatment with Mixture 4F in an Animal Model of Severe Myocardial Infarction The therapeutic efficacy of cells primed with mixture 4F was identified using an animal model of severe myocardial infarction. Specifically, a severe myocardial infarction model was prepared using 7-8 week old nude mice. The severe myocardial infarction model was prepared through left coronary resection, and 5×105 cells per subject were directly transplanted into the ischemic site of the heart. Cardiac function at 28 days of passage after induction of myocardial infarction was evaluated using echocardiography to determine the left ventricle mass, volume [Left ventricle end diastolic diameter (LVEDD), left ventricle end systolic diameter (LVESD)], and left ventricular ejection fraction (LVEF) were measured. In addition, cardiac output and diastolic function of the left ventricle were evaluated in animal models. The results of analysis of echocardiography, cardiac output, and left ventricular diastolic function are shown in FIG. 4A.

Figure 4A:
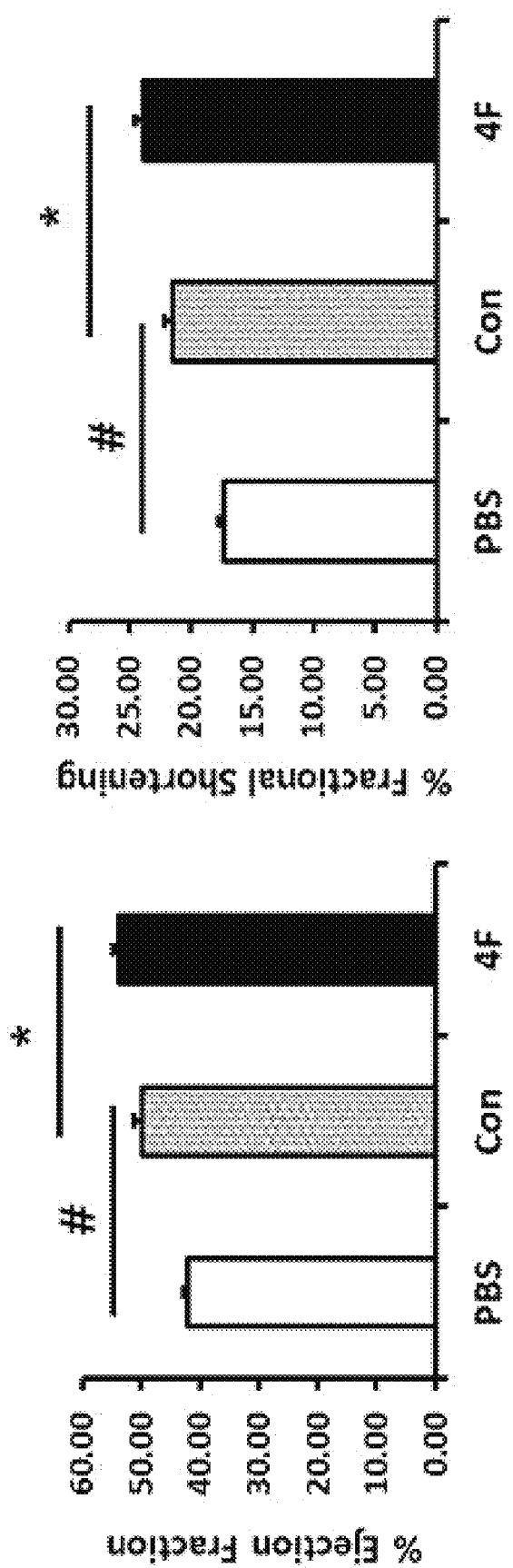
FIG. 4A shows a result of evaluating cardiac function by measuring ejection fraction and fractional shortening at 28 days of passage after induction of myocardial infarction in an animal model of severe myocardial infarction.

As shown in FIG. 4A, the cardiac function evaluation results at 28 days of passage after induction of myocardial infarction showed that the ejection fraction (EF) and fractional shortening (FS) significantly increased in the group treated with mixture 4F compared to the control group. The above results indicate that the mixture 4F further improves the existing vascular stem cell function.

Figure 4B:
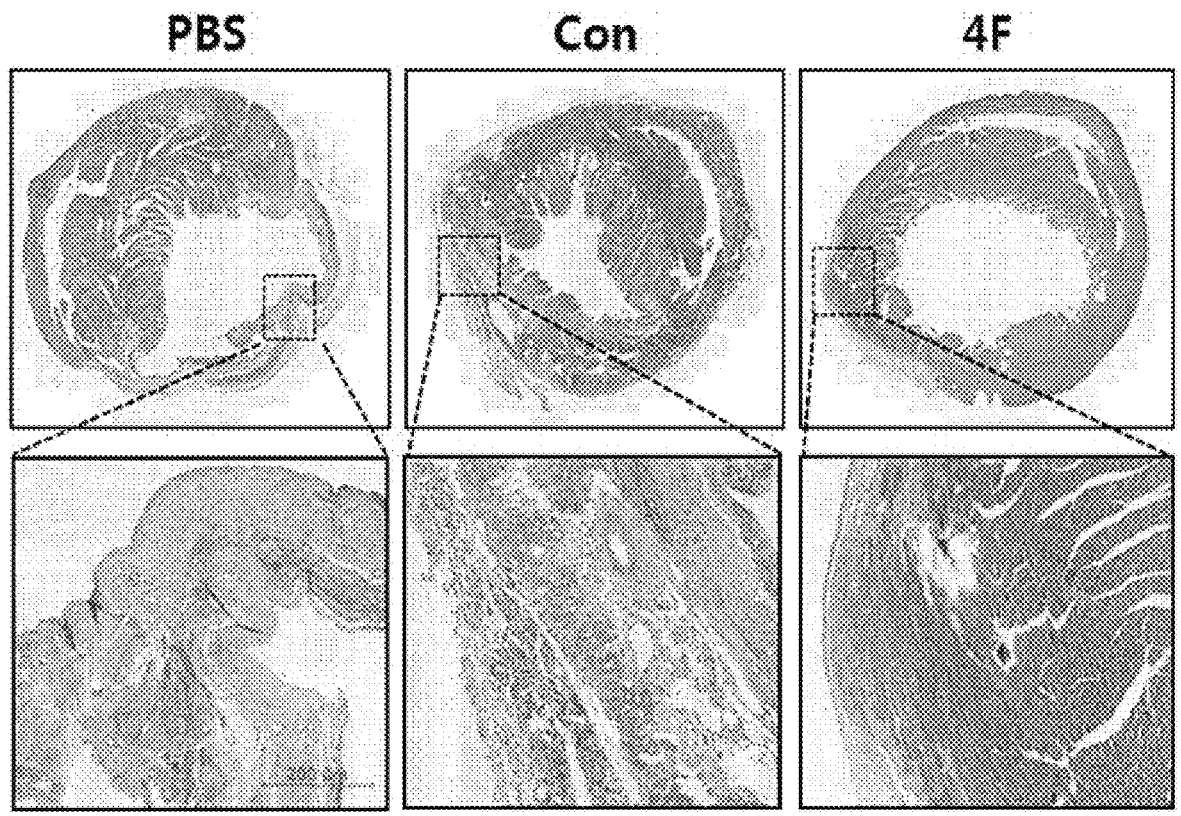
FIG. 4B shows a result of analyzing the degree of myocardial fibrosis by performing Masson's trichrome staining at 28 days of passage after induction of myocardial infarction in an animal model of severe myocardial infarction.
Figure 4B:
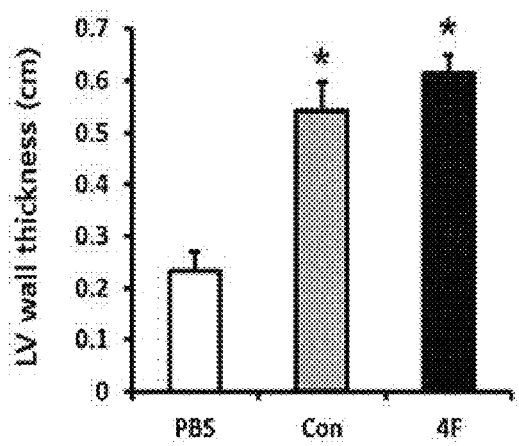
Figure 4B:
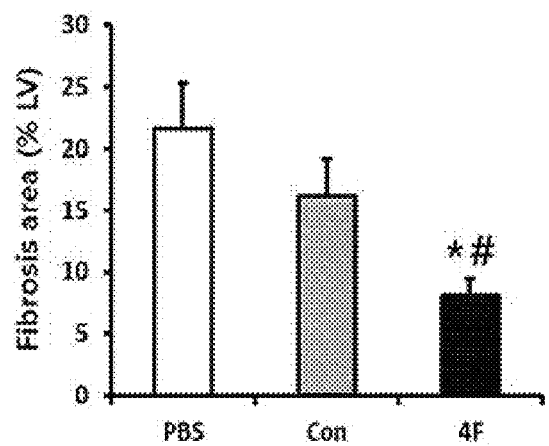

In addition, the degree of myocardial fibrosis (blue stained part) was analyzed by Masson's trichrome staining that can characteristically stain collagen fibers 28 days after the induction of myocardial infarction, and the results are shown in FIG. 4B.

As shown in FIG. 4B, it was identified that the degree of fibrosis of the left ventricle was significantly reduced by the treatment of mixture 4F.

Figure 4C:
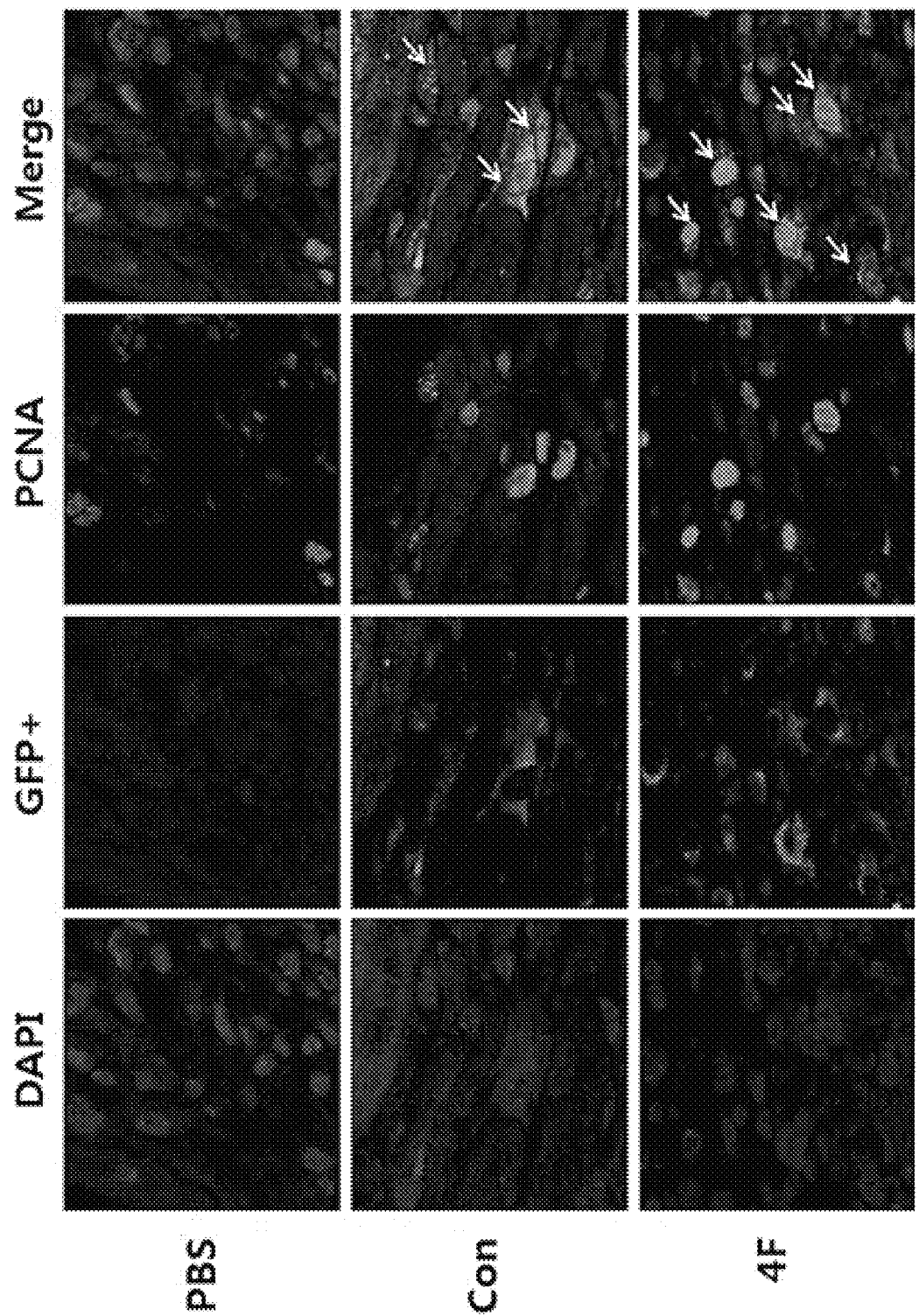
FIG. 4C shows a result of analyzing the engraftment and proliferation rate of cells in myocardium by transplanting GFP-labeled cells into a severe myocardial infarction model and performing immunostaining for PCNA 3 days later.

In addition, 3 days after transplantation of GFP-labeled cells into a severe myocardial infarction model, the engraftment and proliferation rate of cells in myocardium was identified by immunostaining PCNA, a cell proliferation marker, and the results are shown in FIG. 4C.

In FIG. 4C, the expression of PCNA merged with GFP was observed in a large number in the group treated with mixture 4F.

The above results indicate that the vascular stem cells primed with the mixture 4F transplanted in an animal model of severe myocardial infarction promotes myocardial recovery and cardiac function in the heart through proliferation.

Example 6. Analysis of Proliferative Ability, Cell Cycle Change, Cell Senescence and Colony Formation Ability According to the Treatment with Mixture 4F After 10,000 cells were seeded in a 96-well plate for cell proliferation analysis, cell proliferative ability was identified through MTS analysis according to the number of days treated with mixture 4F. In addition, in order to identify the protein expression of CDK inhibitors (p21, p16), which are cell proliferation regulators, intracellular proteins of the control group were isolated, extracted, and quantified using a protein lysis buffer, and then Western blotting was performed using the same amount of protein. Proteins were transferred to a PVDF membrane after SDS-PAGE and blocked in 5% skim milk for 30 minutes. After blocking, the membrane was reacted with each of the primary antibodies p53 (abcam), p27 (abcam), p21 (abcam), p16 (abcam) and b-actin (santacruz) diluted at a ratio of 1:1000 overnight at 4° C. After washing the membrane, it was reacted with the HRP-bound secondary antibody at room temperature for 1 hour, and protein expression was visualized using LAS3000 (Fujifilm). In addition, in order to identify that the decrease in the proliferative ability of cells is due to the cell cycle arrest induced by the increase in undifferentiated characteristics, the cell cycle was analyzed by PI staining and Hst/PY staining. Specifically, PI (santacruz), hoechst 33342 (santacruz), and PY (santacruz) staining were performed on cells cultured to 60-70% confluent, and the cell cycle was analyzed using flow cytometry. The results of identifying the cell proliferation rate and cell cycle change according to the treatment with mixture 4F are shown in FIGS. 5A and 5B.

Figure 5A:
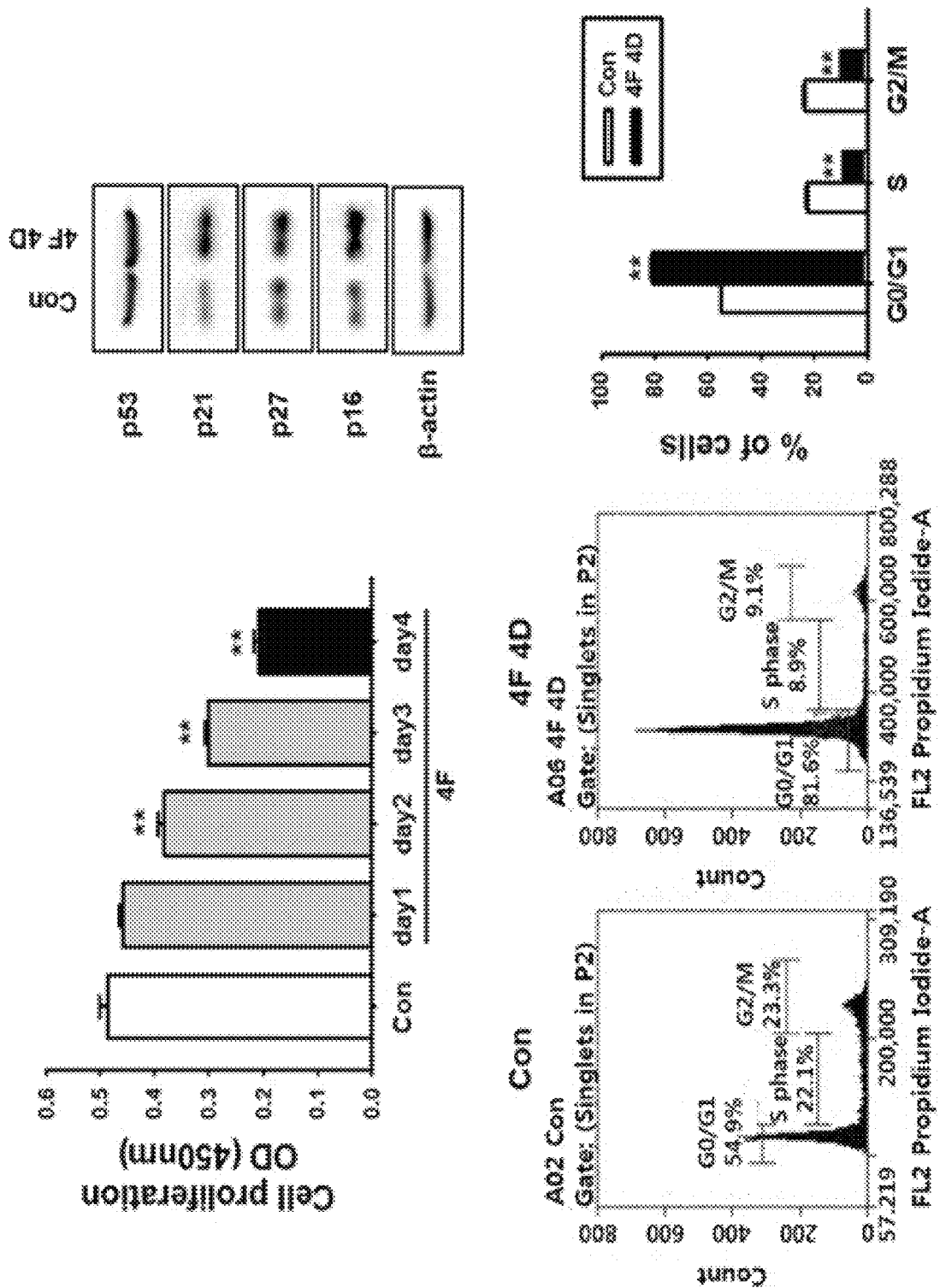
FIG. 5A is a diagram illustrating a result of analyzing the cell proliferation rate change according to the treatment with mixture 4F according to the present disclosure.
Figure 5B:
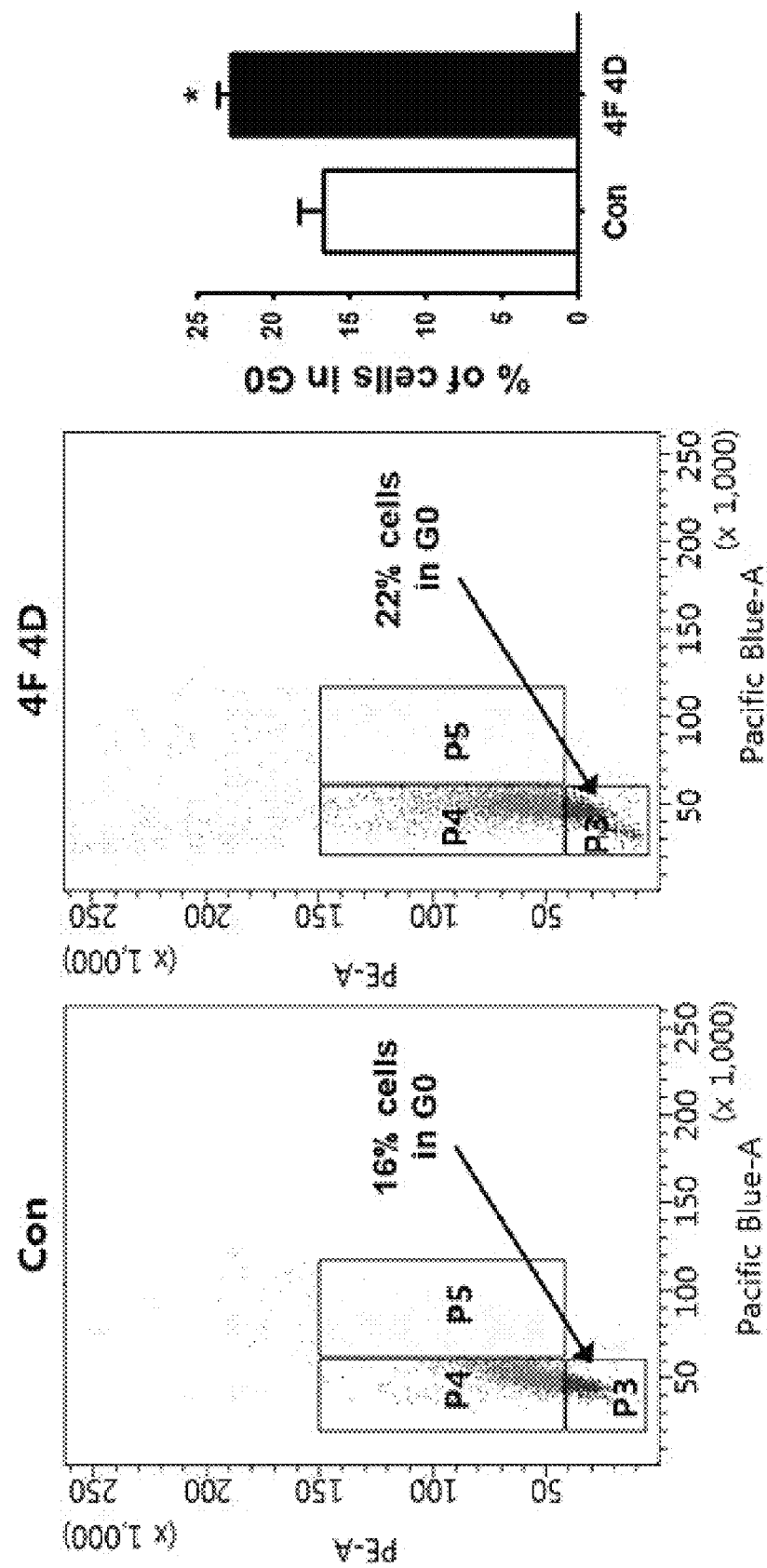
FIG. 5B is a diagram illustrating a result of analyzing the cell cycle change according to the treatment with mixture 4F according to the present disclosure.

As shown in FIGS. 5A and 5B, it was identified that the cell proliferative ability was significantly reduced in a number of days dependent on the treatment of 4F mixture. In addition, it was identified that the protein expression of CDK inhibitors (p21, p16), which are cell proliferation regulators, was significantly increased in the cells treated with mixture 4F. In addition, as a result of cell cycle analysis, it was identified that the S and G2/M phases, where DNA replication and cytoplasmic division occur, were significantly decreased compared to the control group, but the G0/G1 phase was significantly increased when the mixture 4F was treated (day 4). did. In addition, it was identified that when the mixture 4F was treated (day 4), the cell population of the dormant G0 phase was significantly increased compared to the control group.

The degree of senescence of senescent cells (old) was analyzed through cells in which the cell cycle was stopped and repeated passages. Cell senescence analysis was performed using the SA-β-gal assay kit (cell signaling), and was tested according to the manufacturer's manual. The number of senescent cells (β-gal positive-green) per cell group was measured and graphed through microscopic imaging, and the results are shown in FIG. 5C.

Figure 5C:
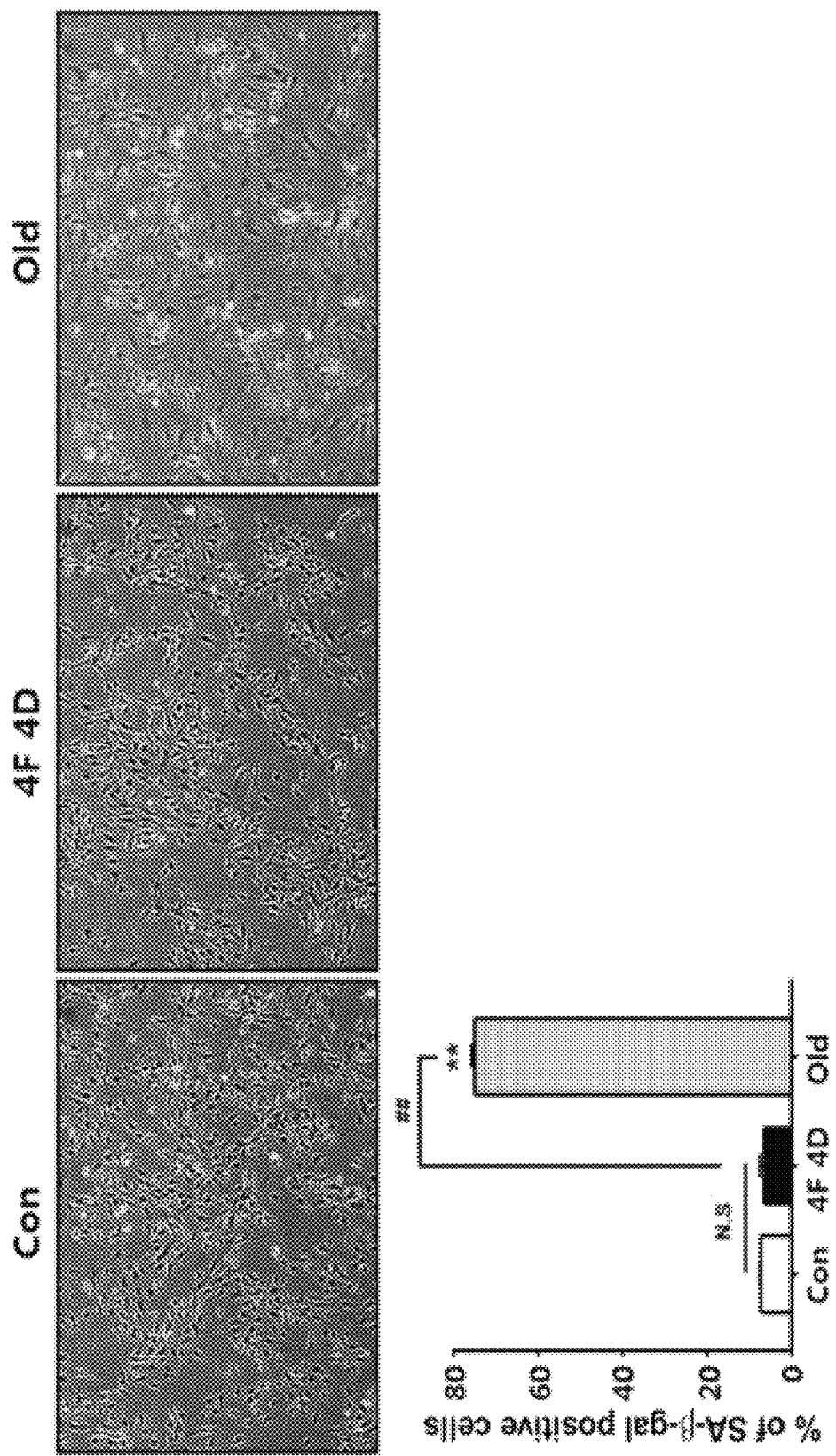
FIG. 5C is a diagram illustrating a result of analyzing the cellular senescence according to the treatment with mixture 4F according to the present disclosure.

As shown in FIG. 5C, it was identified that the cell cycle arrest by the treatment with mixture 4F was induced by an increase in undifferentiated characteristics, not by cell damage or senescence.

In addition, in order to check the colony forming ability of the cells, after coating 1% gelatin in a 96-well plate, the cells were seeded and cultured for 14 to 20 days. Cultured cells were graphed by measuring the number of wells in which colonies were formed through microscopic imaging, which is shown in FIG. 5D.

Figure 5D:
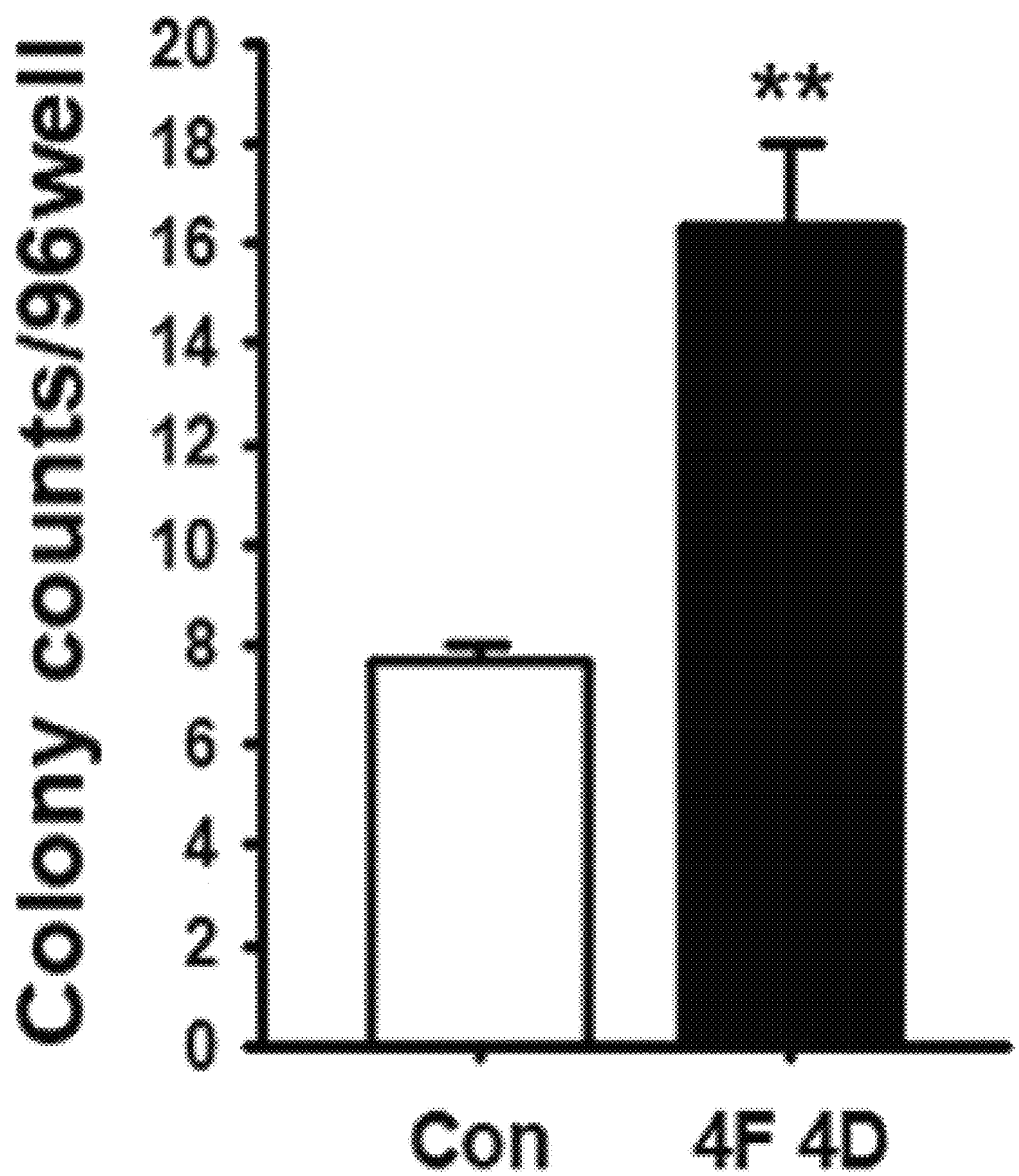
FIG. 5D is a diagram illustrating a result of analyzing the colony forming ability according to the treatment with mixture 4F according to the present disclosure.

As shown in FIG. 5D, as a result of analyzing the colony formation ability of single cells through single cell colony analysis, it was identified that the vascular stem cells fell into a resting state by priming the mixture 4F and the undifferentiated characteristics as stem cells were greatly increased.

Example 7. Gene Expression Analysis Related to Stem Cell Differentiation According to the Treatment with Mixture 4F The expression of undifferentiated or differentiation-related genes in vascular endothelial cells according to the treatment with mixture 4F was measured. Specifically, total RNA was extracted from vascular endothelial cells primed with mixture 4F. 2 μg of total RNA was prepared and RNA sequencing was commissioned by Teragen. Differentially expressed gene (DEG) analysis was performed by extracting a q-value threshold of less than 0.05 based on the Cuffdiff method. The results of analyzing the expression of stem cell differentiation-related genes are shown in FIGS. 6A and 6B.

Figure 6A:
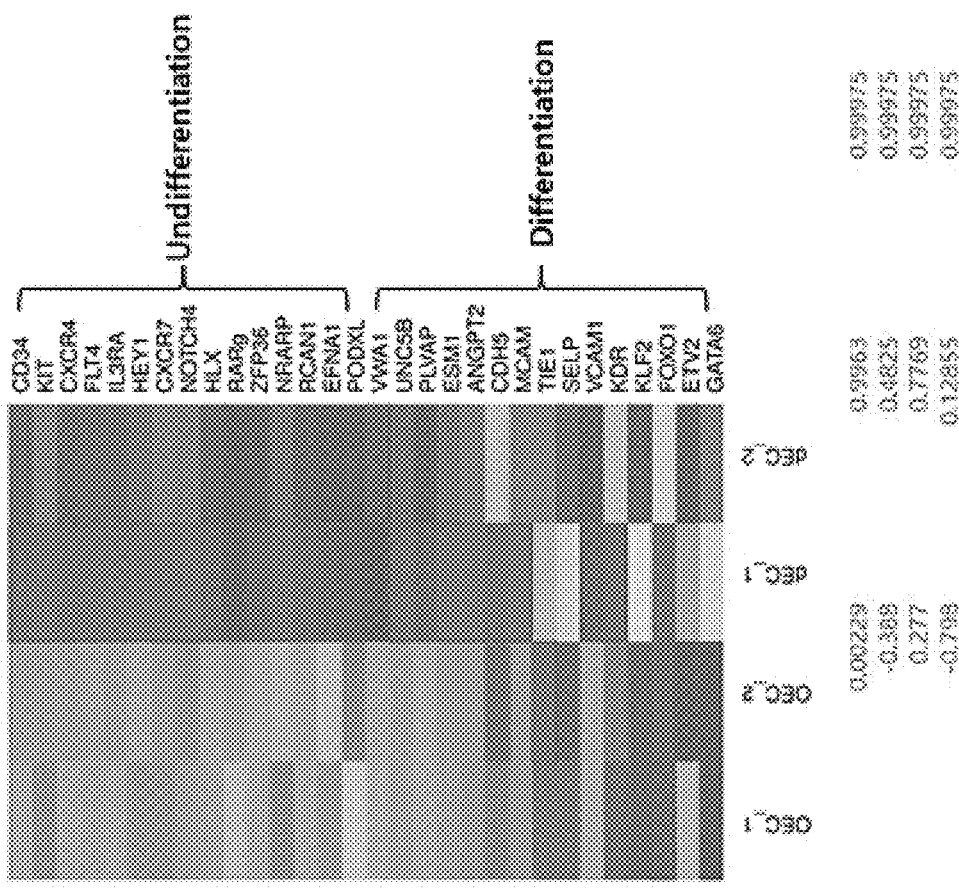
FIG. 6A is a diagram illustrating a result of measuring the gene expression change of the undifferentiated stem cell-related marker according to the treatment with mixture 4F of the present disclosure.

As shown in FIGS. 6A and 6B, as a result of analyzing the transcripts through RNA sequencing, it was identified that cells primed with mixture 4F had clear genetic differences from fully differentiated vascular endothelial cells (HUVECs), and that the expression of some undifferentiated stem cell-related markers (CD34, KIT, HEY1, PODXL, etc.) was significantly increased compared to outgrowing ECs (OEC, L-EPC). It was identified that the expression of differentiated vascular endothelial cell-specific genes was also reduced to a level similar to that of outgrowing ECs (OEC, L-EPC) or slightly decreased. These results indicate that cells primed with mixture 4F acquire immature characteristics.

Example 8. Analysis of Apoptosis Rate of Undifferentiated Stem Cells According to the Treatment with Mixture 4F Undifferentiated stem cells have higher viability due to their protective ability against pathophysiological environments such as ischemic stimulation, and thus have higher transplantation and engraftments than differentiated cells. In order to identify this, the cell death rate was analyzed by implementing the ischemic state (non-nutrient and hypoxic state) in vitro. For cell death rate analysis, each cell group was cultured for 24 hours in a nutrient-free medium from which FBS, growth factors and cytokines were removed, and under hypoxic conditions of 1% O2, and the ischemia state was implemented in vitro. Thereafter, flow cytometry was performed using an annexin V/PI staining kit (BD Biosciences), and the results are shown in FIG. 7.

Figure 7:
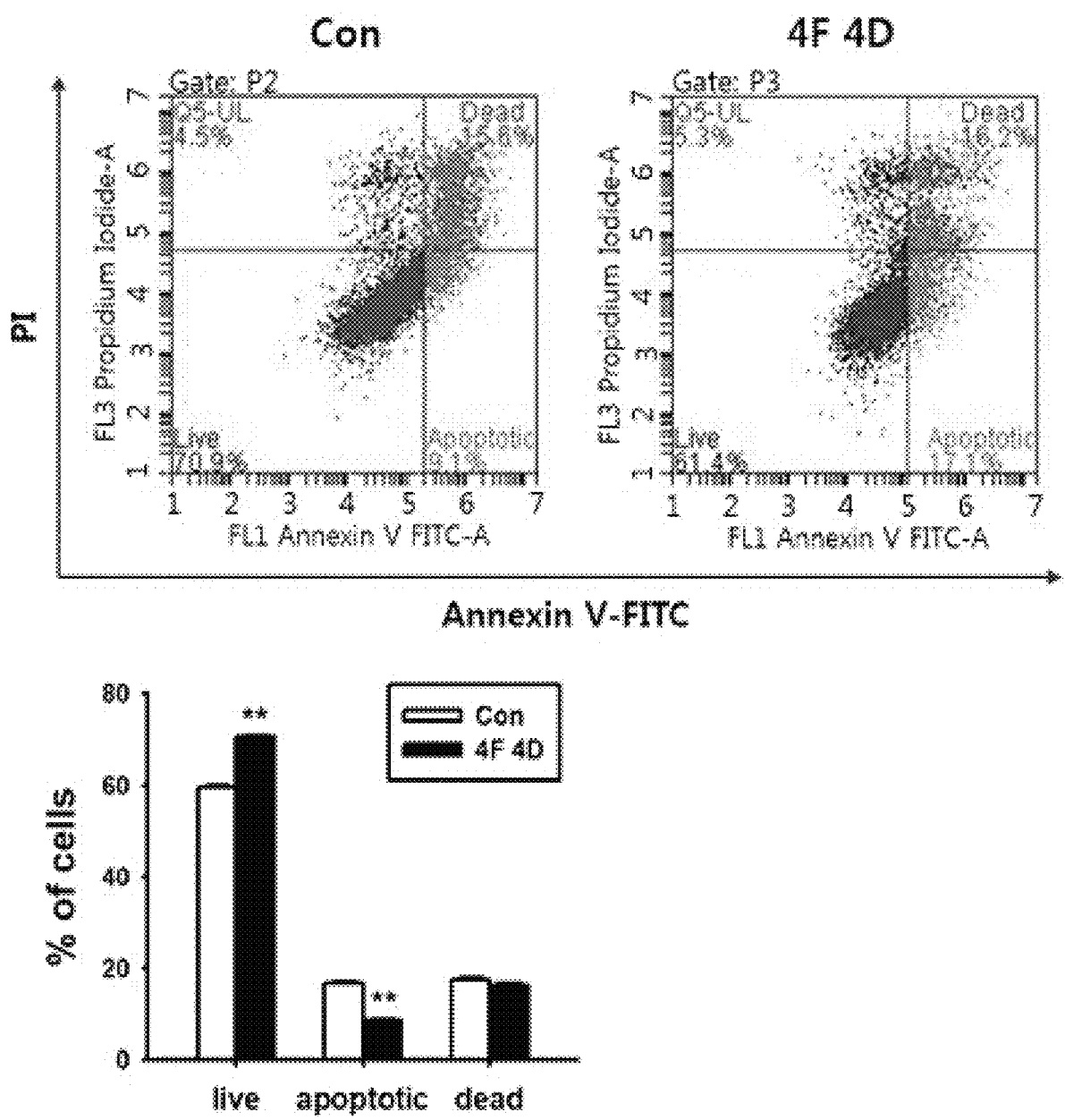
FIG. 7 is a diagram illustrating a result of analyzing the apoptosis rate of undifferentiated stem cells according to the treatment with mixture 4F of the present disclosure.

As shown in FIG. 7, it was identified that the viable cell population of the cells primed with the mixture 4F was significantly increased compared to the control group. The above results indicate that the treatment with mixture 4F increases the undifferentiated characteristics of cells, which contributes to the improvement of cell viability by enhancing the defense mechanism against ischemic stimulation.

Example 9. Analysis of Proliferation Rate and Marker Expression of Undifferentiated Stem Cells According to the Treatment with Mixture 4F Recovery of cell proliferative ability and marker expression was analyzed when cells whose cell cycle was stopped by treatment with mixture 4F were reperfused with a nutrient medium (b-FGF, EGF, IGF-1, and ascorbic acid added) used for conventional cell culture. Specifically, the mixture 4F was treated for 4 days and the cells in which the cell cycle was stopped were cultured (reperfusion) for 5 days in a nutrient medium (b-FGF, EGF, IGF-1, ascorbic acid added) conditions. The recovery of the proliferative ability of the cells on the 3rd and 5th days after replacement with the nutrient medium was identified using the MTS assay kit. The MTS analysis was performed according to the manufacturer's manual. The cell proliferation rate is shown in FIG. 8A, and the results of marker expression analysis are shown in FIGS. 8B and 8C.

Figure 8A:
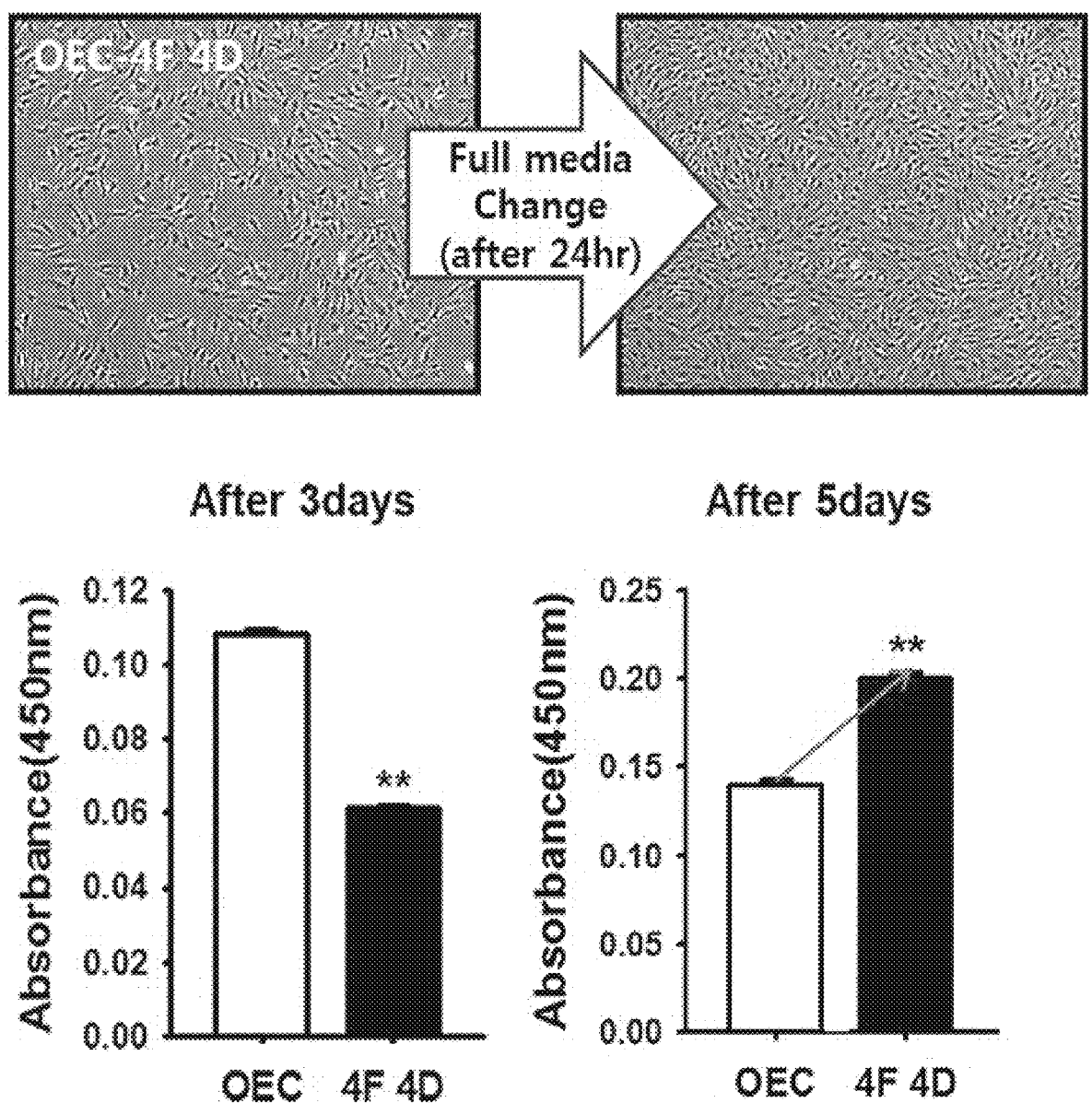
FIG. 8A is a diagram illustrating the analysis of the proliferation rate of undifferentiated stem cells according to the treatment with mixture 4F of the present disclosure.
Figure 8B:
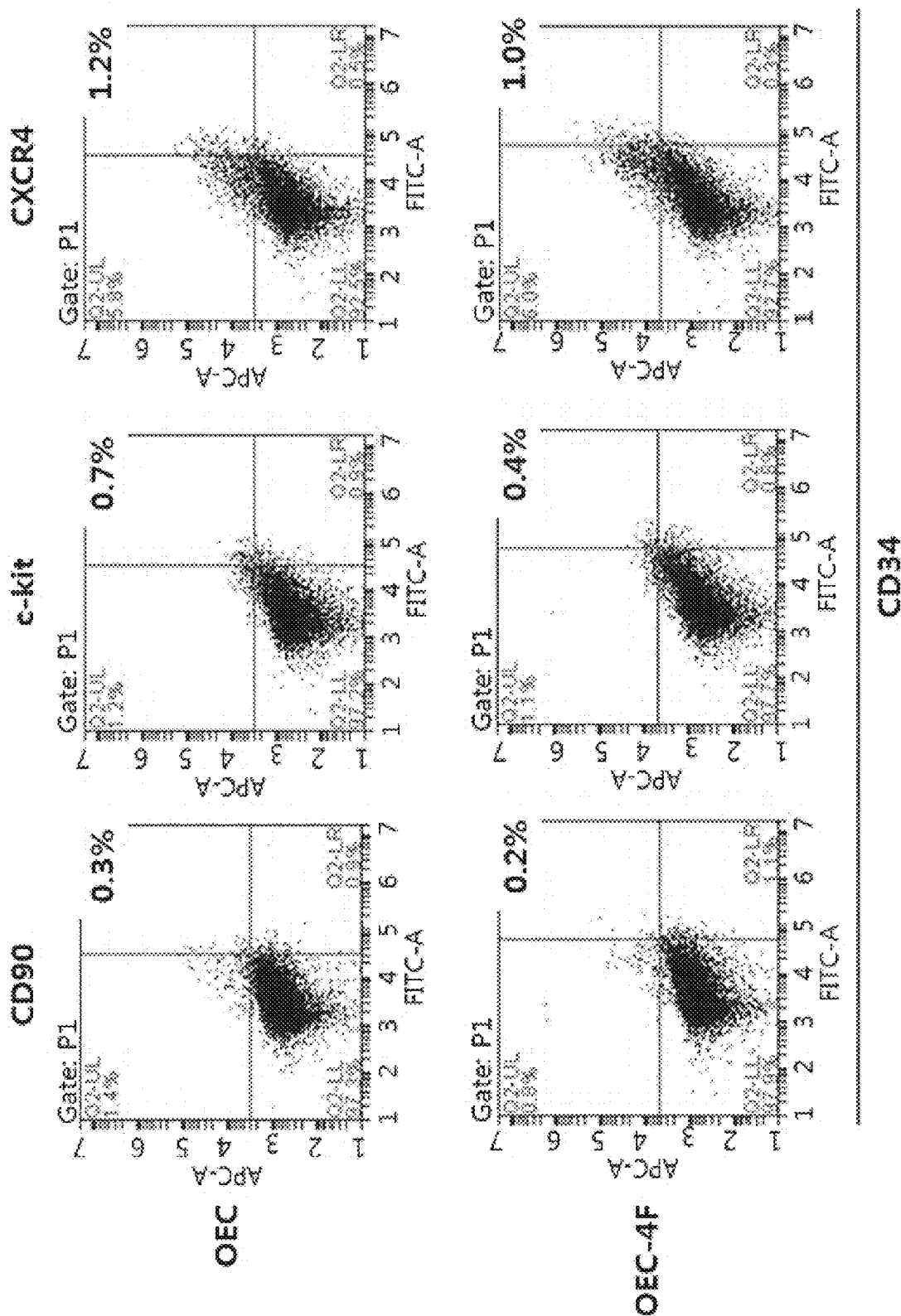
FIGS. 8B and 8C are diagrams illustrating the results of analysis of marker expression of undifferentiated stem cells according to the treatment with mixture 4F of the present disclosure.
Figure 8C:
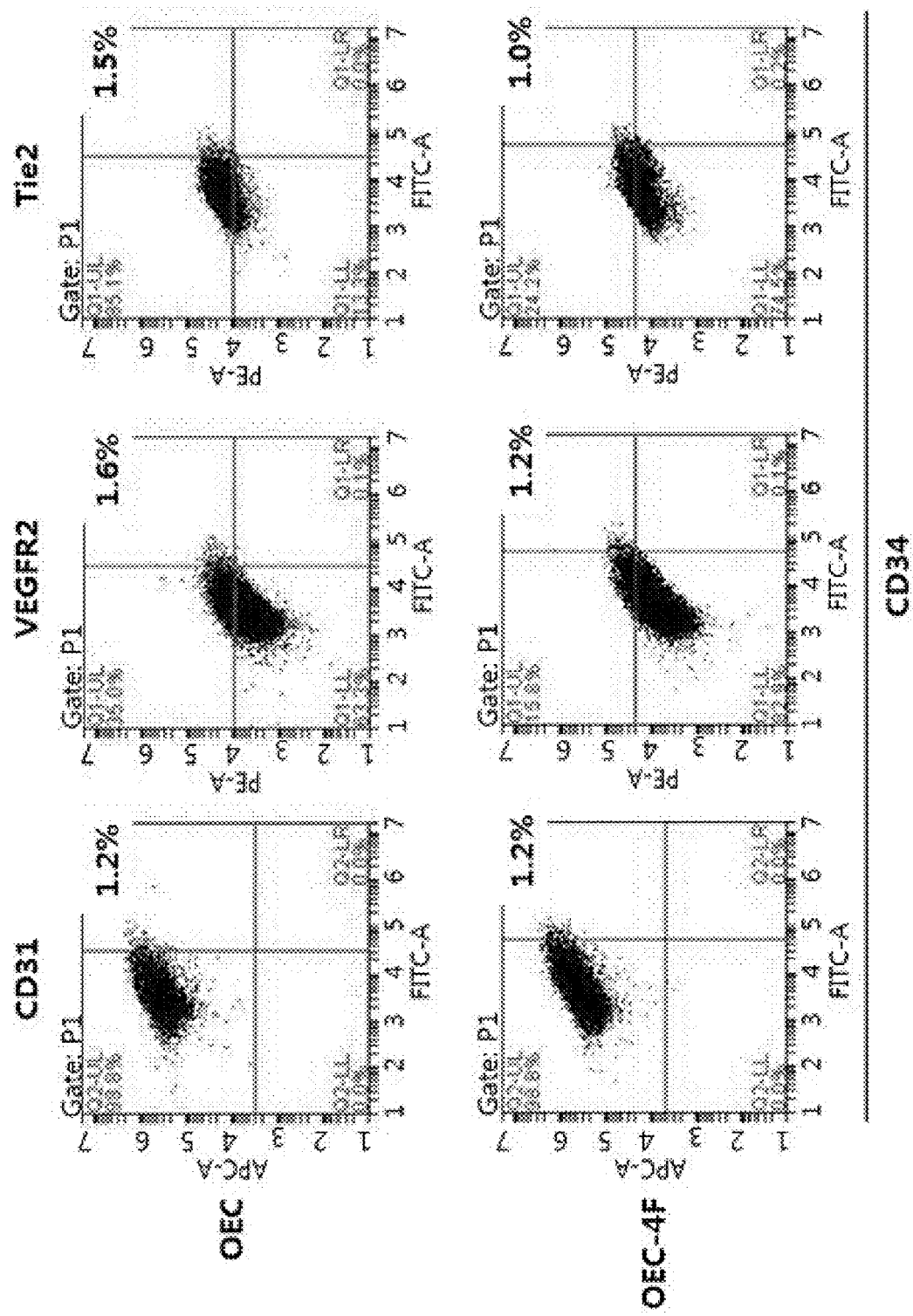
Figure 9A:
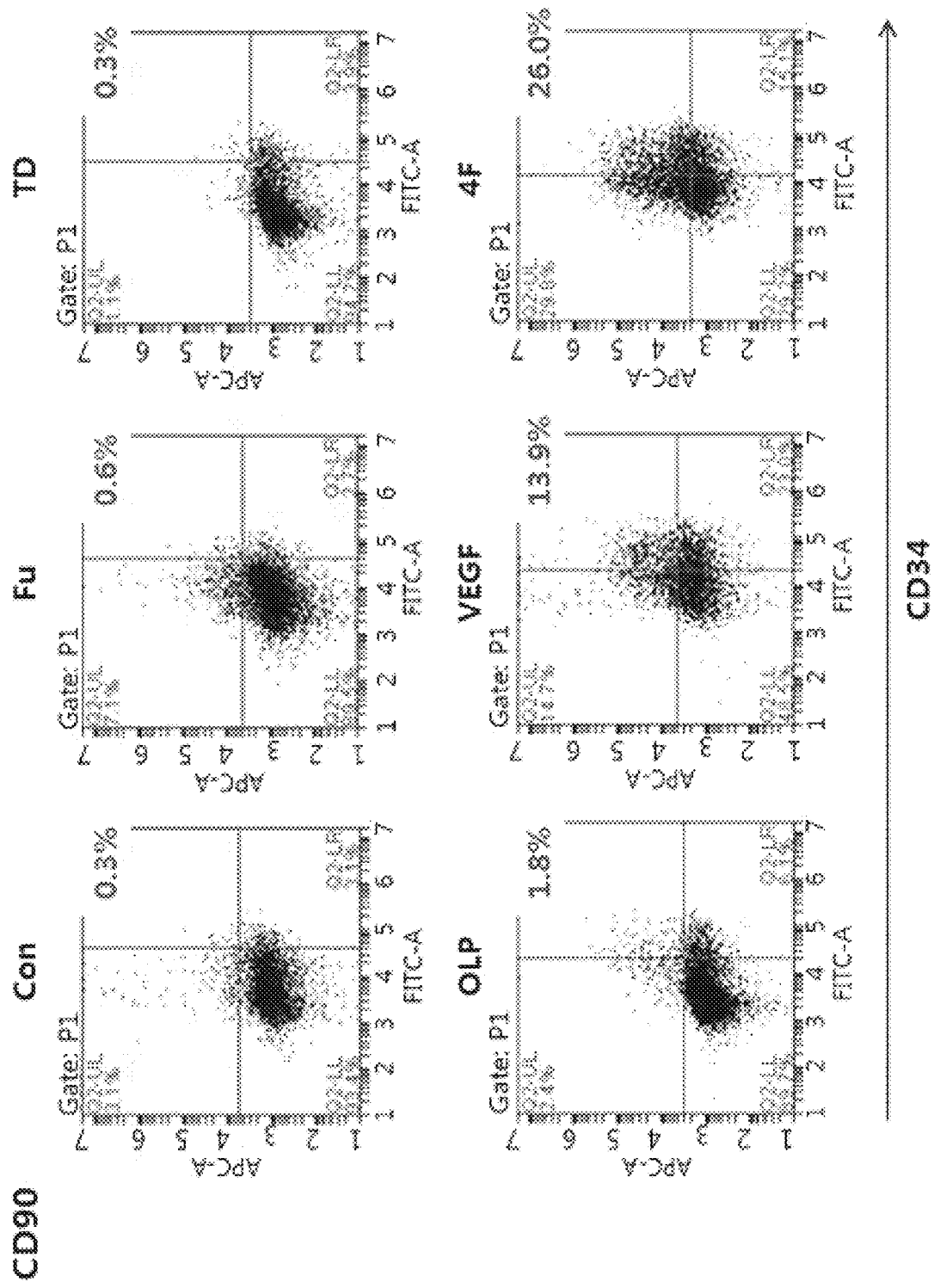
FIGS. 9A to 9E are diagrams illustrating the results of analysis of marker expression according to the treatment with mixture 4F or a single component of the present disclosure.
Figure 9B:
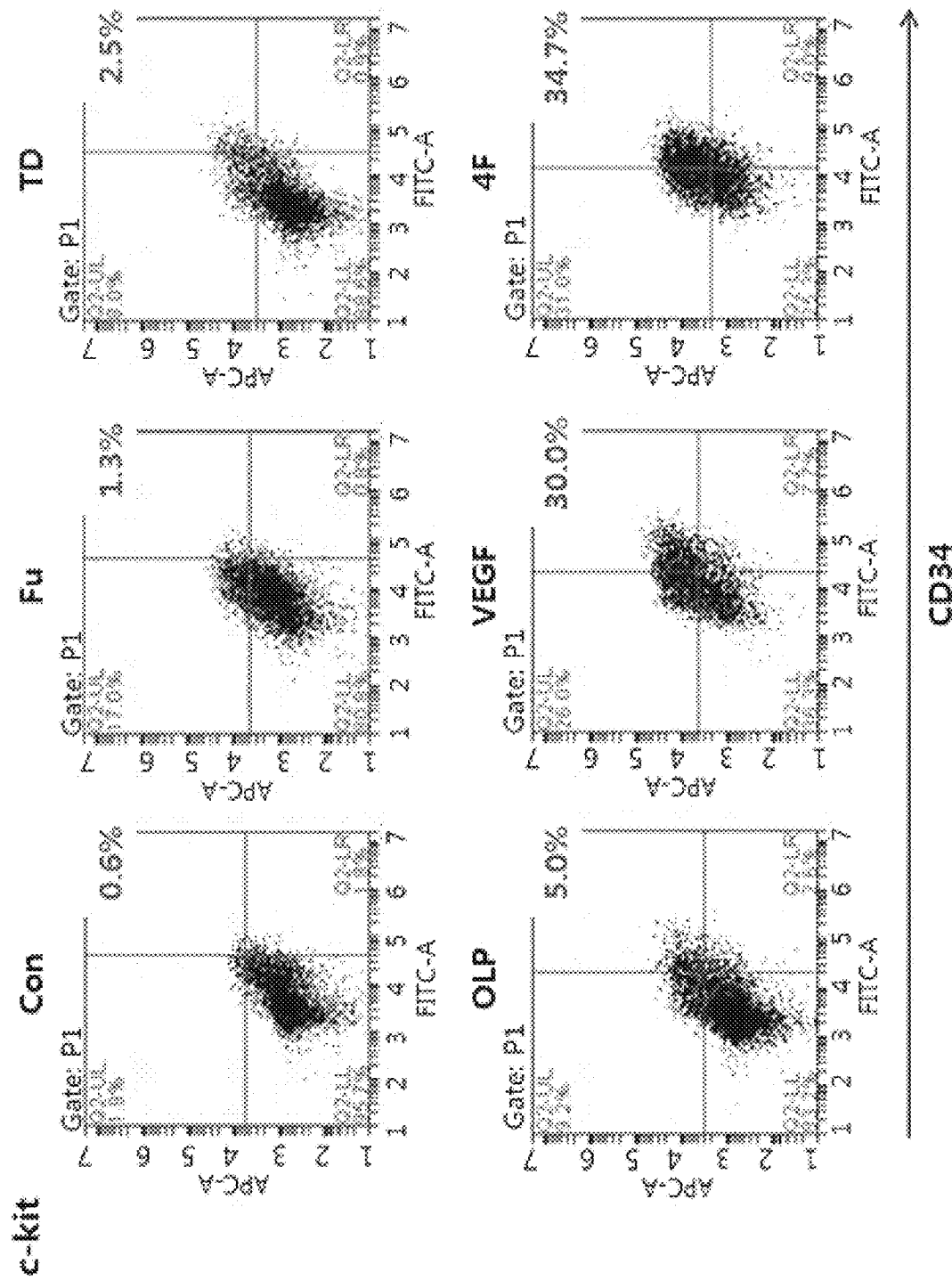
Figure 9C:
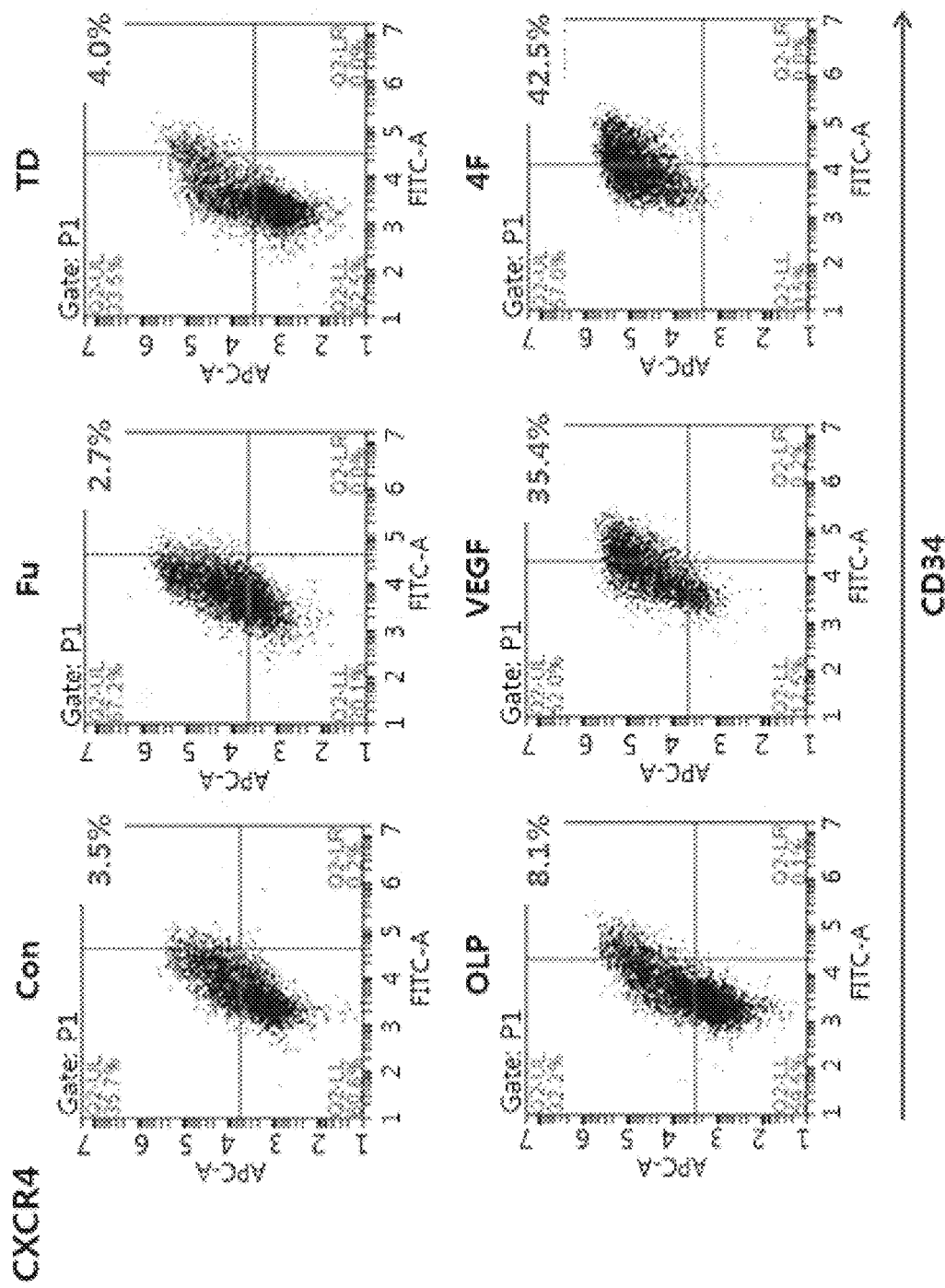
Figure 9D:
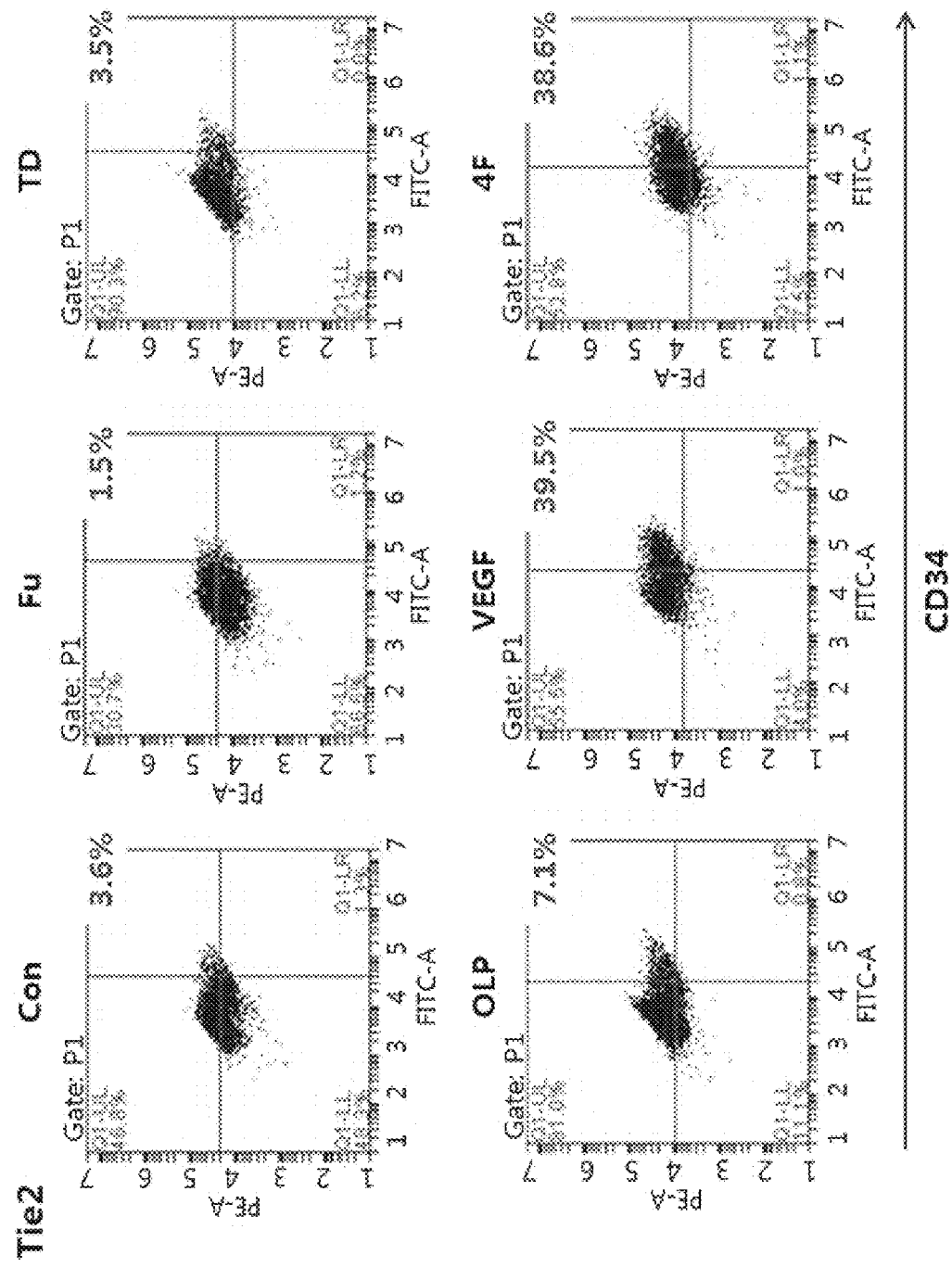
Figure 9E:
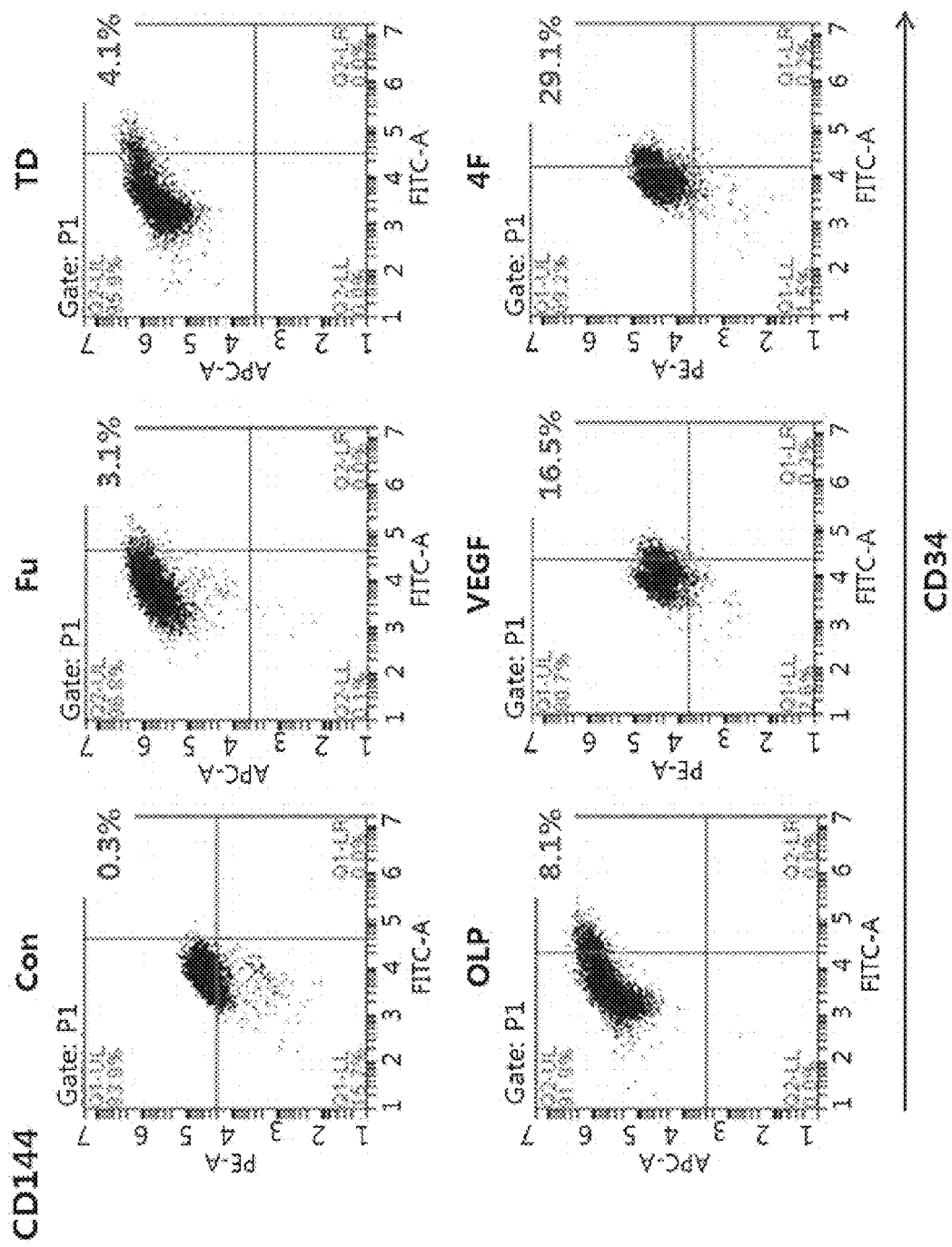

As shown in FIGS. 8A to 8C, it was identified that the cells primed with the mixture 4F not only recovered the proliferative ability, which had been reduced by reperfusion of the nutrient medium, but also the expression of the markers to a level similar to that of the control group. From the above results, it was identified that the cell cycle arrest caused by the treatment with mixture 4F and the resulting decrease in cell proliferative ability is not irreversible phenomena such as cell damage or senescence, but are general characteristics of resting cells that appear along with the increase in the undifferentiated nature of the cells, and is a reversible phenomenon that may be sufficiently recovered by necessary stimulus.

Example 10. Comparison of Marker Expression and Angiogenic Ability According to the Treatment with Mixture 4F or a Single Component The marker expression and angiogenic ability were compared according to the treatment with mixture 4F or a single component (fucoidan, a tauroursodeoxycholic acid, oleuropein, and a vascular endothelial growth factor). The experimental group of this experiment was treated with mixture 4F. As a control group, an untreated group (con), a group treated with fucoidan (Fu, 0.1 μg/ml), a group treated with a tauroursodeoxycholic acid (TD, 25 μM), a group treated with oleuropein (OLP, 0.5 μM), and a group treated with a vascular endothelial growth factor (VEGF, 100 ng/ml) were used.

First, the expression of markers, i.e., CD90, c-kit, CXCR4, Tie2 and CD144, of cells primed with mixture 4F was analyzed by the method of Example 1, and the results are shown in FIGS. 9A to 9E, respectively.

As shown in FIGS. 9A to 9E, it was identified that the cell population expressing undifferentiated markers (CD34, CD90, c-kit, and CXCR4) increased significantly in the group treated with mixture 4F compared to a single treatment condition of each component.

For angiogenesis analysis, 60 μl of Matrigel GFR (BD Biosciences) was added to a 96-well plate to harden, and then 10,000 cells were seeded and cultured. After 6 hours of culture, the degree of tube-like network formation was observed under a microscope. The results of microscopic observation were graphed for angiogenic ability of cells through branch number counting formed using Image J software, and the results are shown in FIG. 10.

Figure 10:
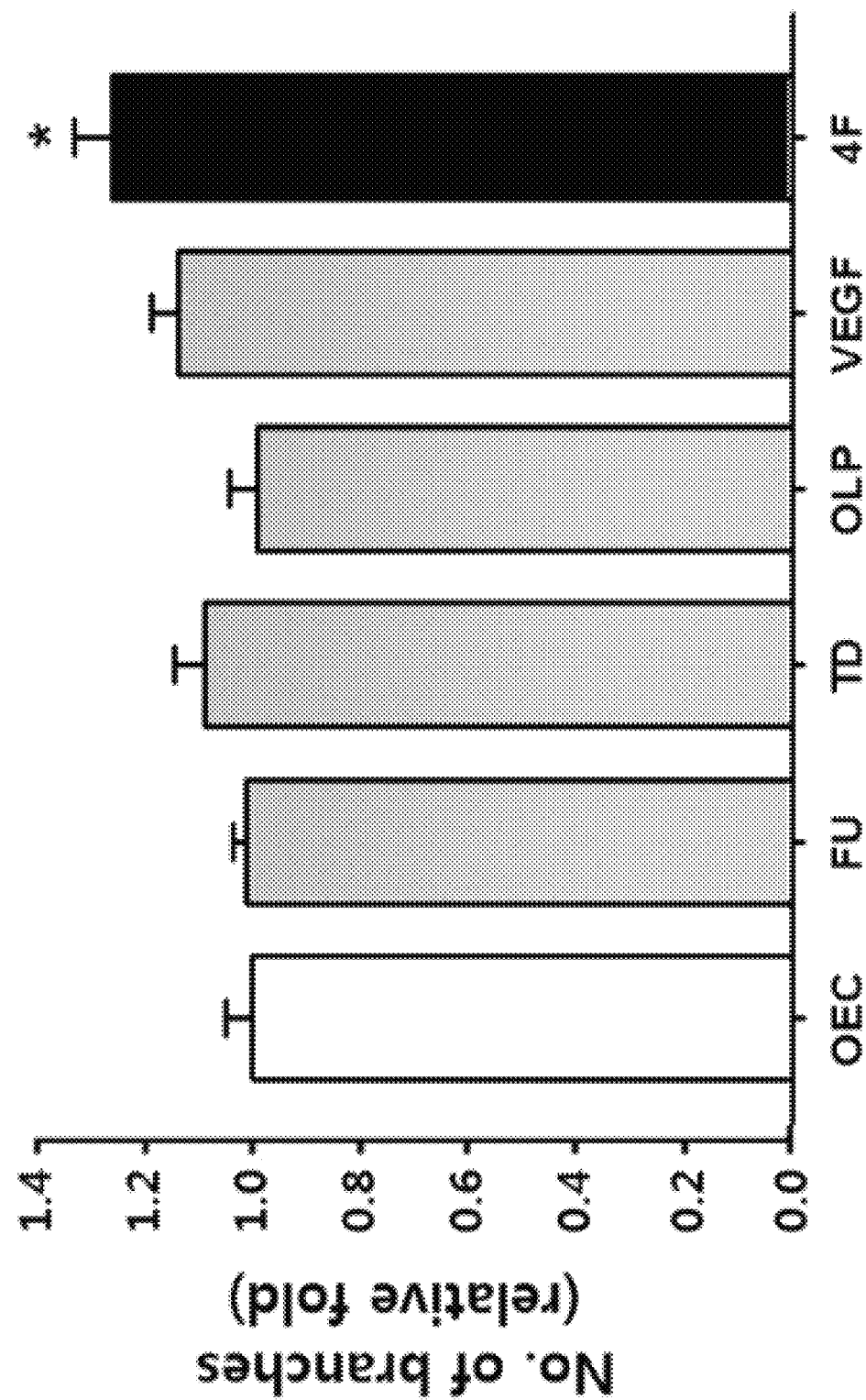
FIG. 10 is a diagram illustrating a result of analyzing the angiogenic ability according to the treatment with mixture 4F or a single component of the present disclosure.

As shown in FIG. 10, it was identified that the group treated with mixture 4F significantly increased the angiogenic ability compared to the single treatment condition of each component.

These results indicate that the treatment with mixture 4F significantly increased the undifferentiated characteristics and angiogenic ability of cells compared to the treatment with a single component.

Example 11. Xeno-Free Culture Method Using Mixture 4F

Figure 11:
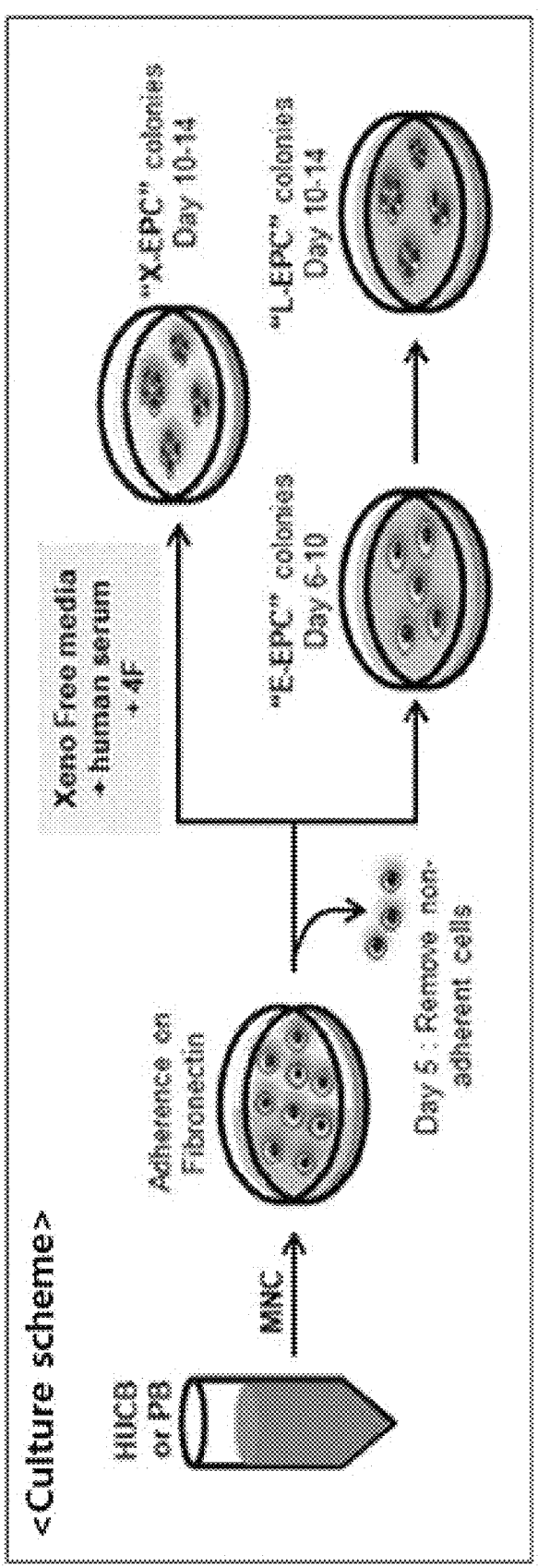
FIG. 11 is a diagram schematically illustrating a xeno-free culture method using mixture 4F according to the present disclosure.

FIG. 11 is a diagram schematically illustrating a xeno-free culture method using mixture 4F. Specifically, the isolation and culture of vascular endothelial cells (EPC) is performed by density difference centrifugation using ficoll after receiving umbilical cord blood (IRB approval number 05-2017-053, 50 cc or more) of mothers who visited the Department of Obstetrics and Gynecology, Pusan National University, Yangsan to obtain monocytes (MNCs). After red blood cell lysis, the cells were seeded ($7 \times 10^6$ cells/well) in a 6-well plate coated with fibronectin (1 μg/cm$^2$), and were cultured for 5 days in an atmosphere of 5% $CO_2$ at 37° C. under conditions of each medium (xeno-free medium containing mixture 4F or a known medium for vascular endothelial cell differentiation (EGM2 media)). The xeno-free medium containing the mixture 4F excludes cytokines or growth factors and animal serum (FBS) added to the existing culture medium, and only mixture 4F and human serum (2%) are added to the basal medium. After culture, the medium was exchanged every day, and the EPC colony attachment was identified and subcultured when 70% or more thereof is under a confluent state. According to the type of culture medium, the cells obtained by culturing with the conventional vascular endothelial cell differentiation medium are named "L-EPC," and the cells obtained by culturing with a xeno-free medium containing mixture 4F are named "X-EPC."

Example 12. Identification of Morphological Characteristics of Vascular Stem Cells Cultured by the Xeno-Free Culture Method Using Mixture 4F For morphological comparison of cells, the morphological characteristics of cells were identified by microscopic imaging under a 70 to 80% confluence state. Specifically, as for endothelial cell lineage-specific functional evaluation, Ac-LDL uptake and UEA-1 binding assay, cells cultured under a 10-20% confluence state were cultured in serum starvation for 2 hours. The cultured cells were treated with Ac-LDL (Invitrogen) at a concentration of 10 μg/ml, and then reacted at 37° C. for 4 hours. The reacted cells were fixed at room temperature for 10-15 minutes using 4% PFA, and reacted at room temperature for 1 hour at a concentration of 10 μg/ml UEA-1 (sigma aldrich). The reacted cells were washed with PBS, stained with DAPI staining, and observed with a fluorescence microscope. The results of analyzing the morphological characteristics of vascular stem cells cultured by the xeno-free culture method using mixture 4F are shown in FIG. 12.

Figure 12:
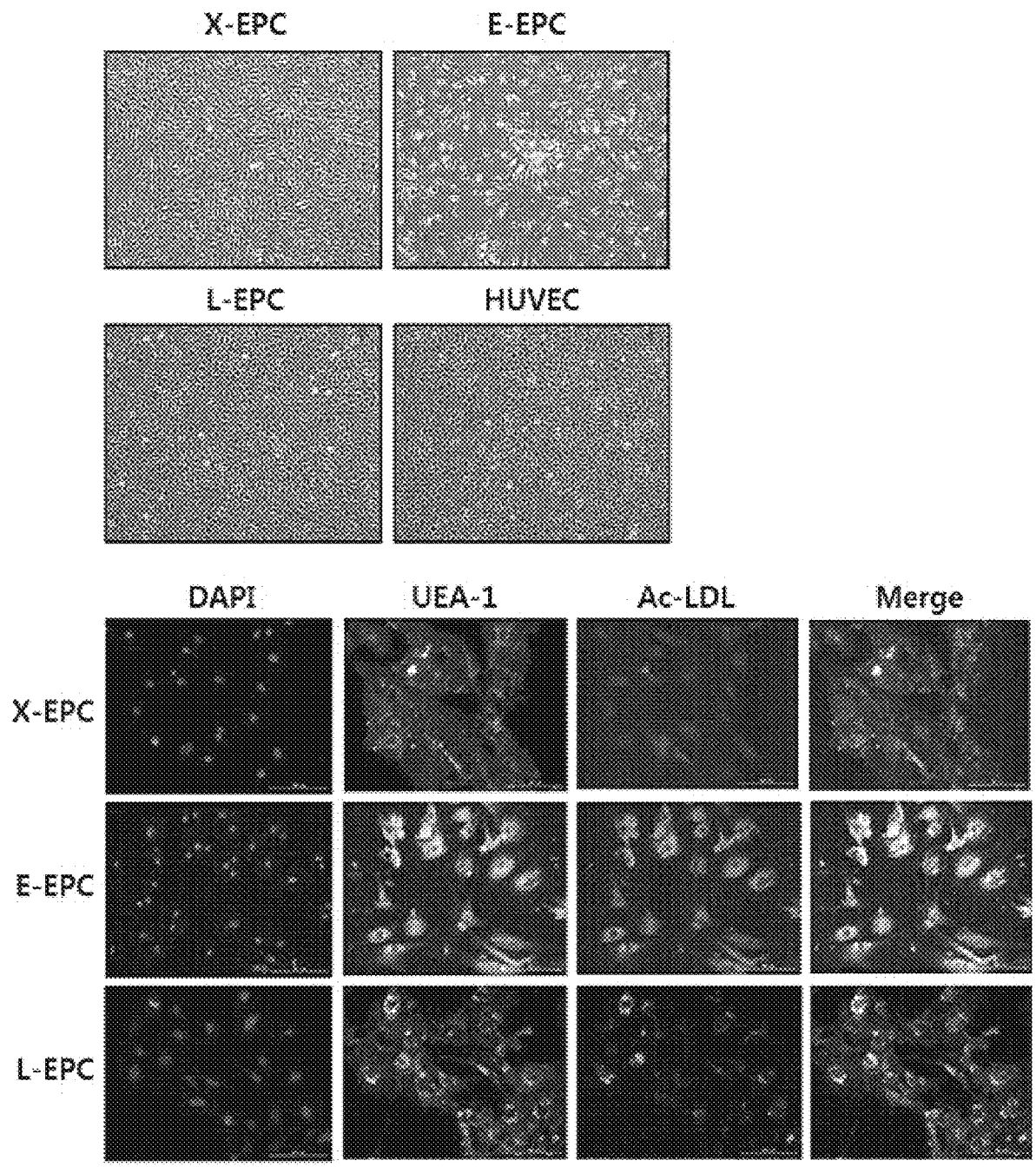
FIG. 12 is a diagram illustrating a result of identifying the morphological characteristics of the vascular stem cells cultured by the xeno-free culture method using mixture 4F according to the present disclosure.

FIG. 12 identifies that the cells (X-EPC) cultured by the xeno-free culture method using mixture 4F had the same phenotype as the cells (E-EPC, L-EPC) cultured by the conventional culture method. In addition, it was identified that there was no specific morphological change of the cells by the xeno-free culture method using mixture 4F.

Example 13. Analysis of Gene Expression of Undifferentiated Stem Cell-Related Markers in Vascular Stem Cells Cultured in the Xeno-Free Culture Method Using Mixture 4F The expression of hematopoietic linage markers (CD11b, CD14, CD45), undifferentiated markers (CD34, c-kit, CXCR4), and endothelial linage markers (VEGFR2, PECAM, VE-cadherin) of the cells cultured in Example 11 were analyzed. Specifically, the cells cultured in Example 11 were reacted with trypsin-EDTA at 1:100, 4° C. for 30 minutes, and removed from the culture plate. The expression of the undifferentiated stem cell-related marker gene of the cells was analyzed by flow cytometry, and the results are shown in FIG. 13.

Figure 13:
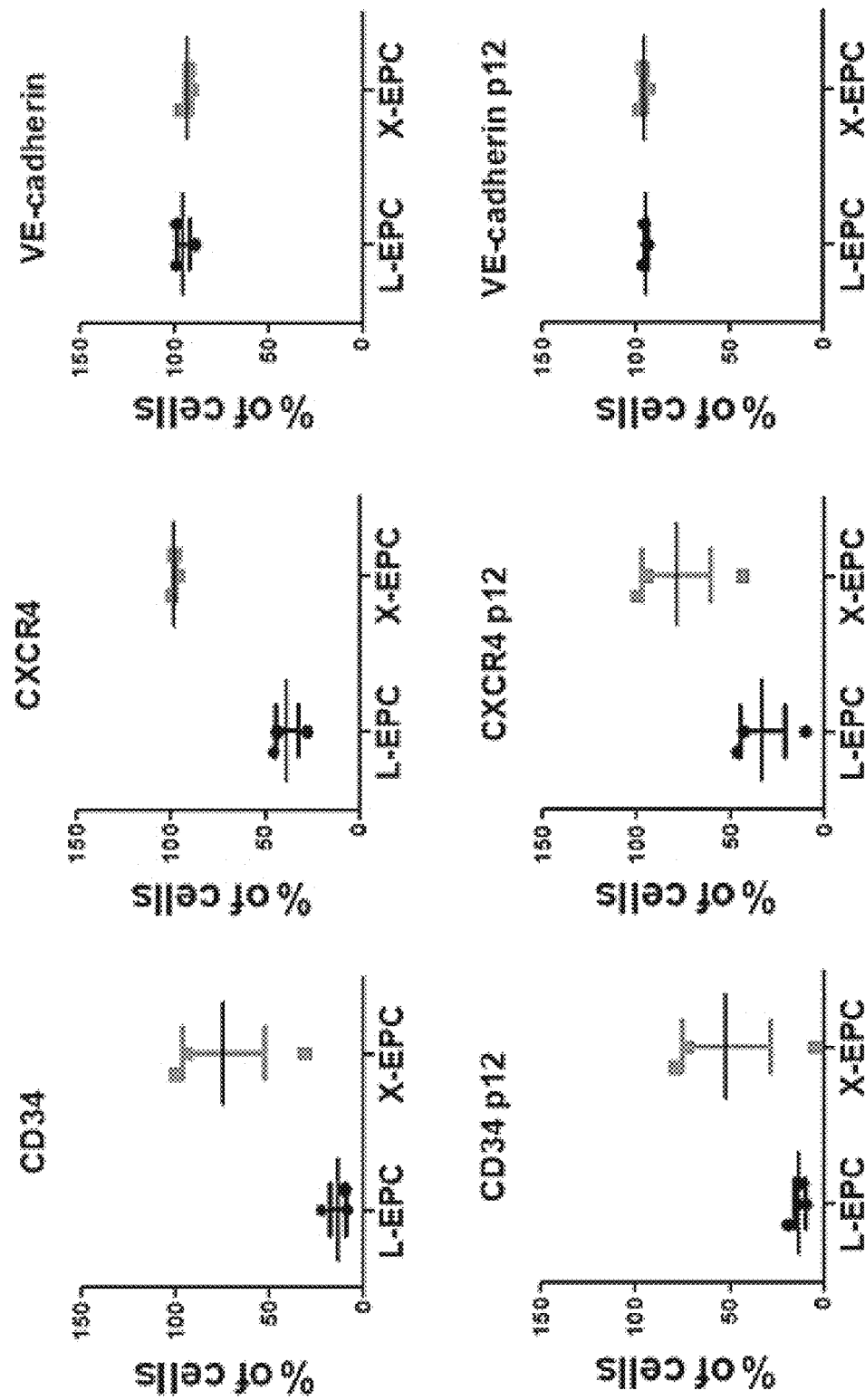
FIG. 13 is a diagram illustrating a result of analyzing the gene expression of the undifferentiated stem cell-related marker of vascular stem cells cultured by the xeno-free culture method using mixture 4F according to the present disclosure.

As shown in FIG. 13, the expression of hematopoietic linage markers (CD11b, CD14, CD45) was hardly identified in the cells (X-EPC) cultured by the xeno-free culture method using mixture 4F compared to the cell group (E-EPC, L-EPC, HUVEC) obtained by the conventional culture method. It was identified that the expression of the undifferentiated marker and the marker of the vascular endothelial cell linage was maintained high (3 lots for each umbilical cord blood donor were secured, The expression of representative markers CD34, CXCR4, and VE-cadherin was maintained higher than that of L-EPC even after continuous subculture). Thus, it was identified that the cells (X-EPC) obtained by the xeno-free culture method using mixture 4F were vascular stem cells with higher undifferentiated characteristics than the cells cultured by the conventional culture method.

Example 14. Analysis of Proliferative Ability, Cell Cycle Change and Colony Formation Ability of Vascular Stem Cells Cultured by the Xeno-Free Culture Method Using Mixture 4F Cells cultured by the xeno-free culture method using mixture 4F according to the method of Example 11 were separated into single cells, and proliferative ability, cell cycle change, and colony formation ability were analyzed in the same manner as in Example 6. For the control group of this example, cells cultured by the conventional culture method (L-EPC) and cells cultured in a medium containing each single component in a xeno-free medium [a group treated with fucoidan (Fu, 0.1 µg/ml), a group treated with a tauroursodeoxycholic acid (TD, 25 µM), a group treated with oleuropein (OLP, 0.5 µM), and a group treated with a vascular endothelial growth factor (VEGF, 100 ng/ml)] were used. The results of analyzing the colony formation ability are shown in FIGS. 14A and 14B.

Figure 14A:
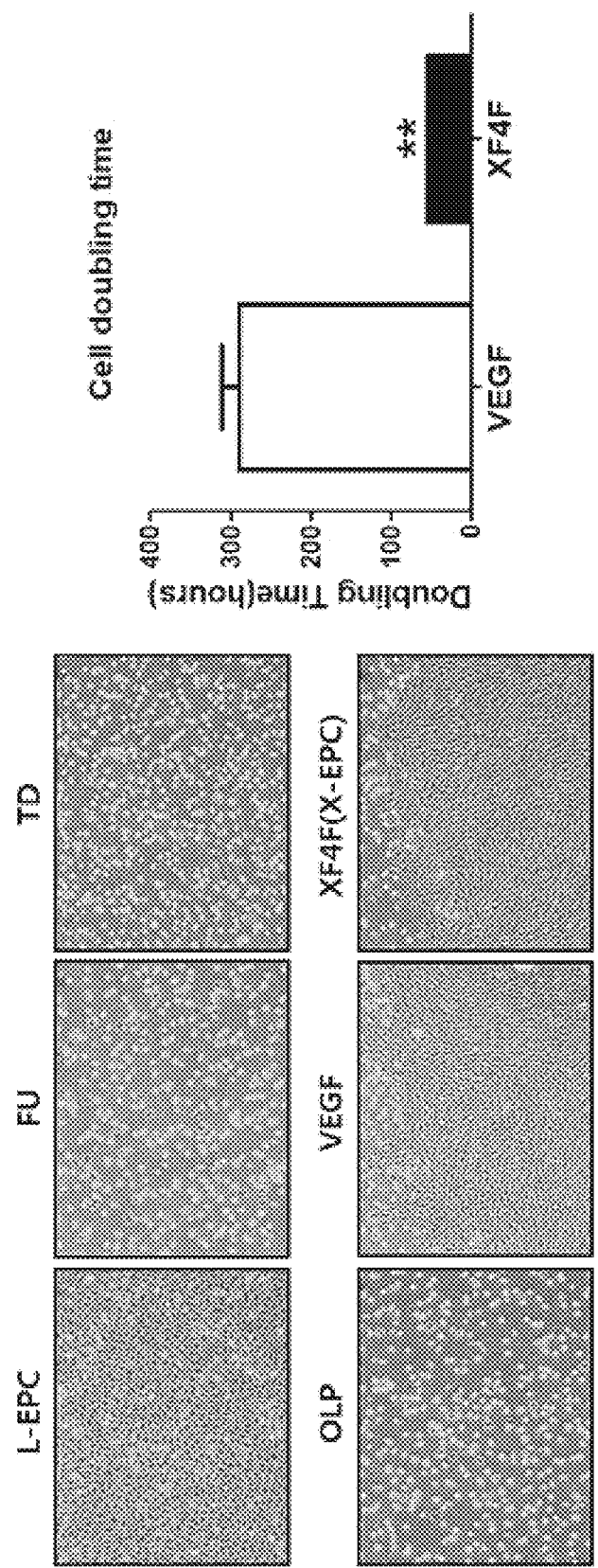
FIG. 14A is a diagram illustrating a result of analyzing the proliferative ability and colony formation ability of vascular stem cells cultured by the xeno-free culture method using mixture 4F according to the present disclosure.
Figure 14B:
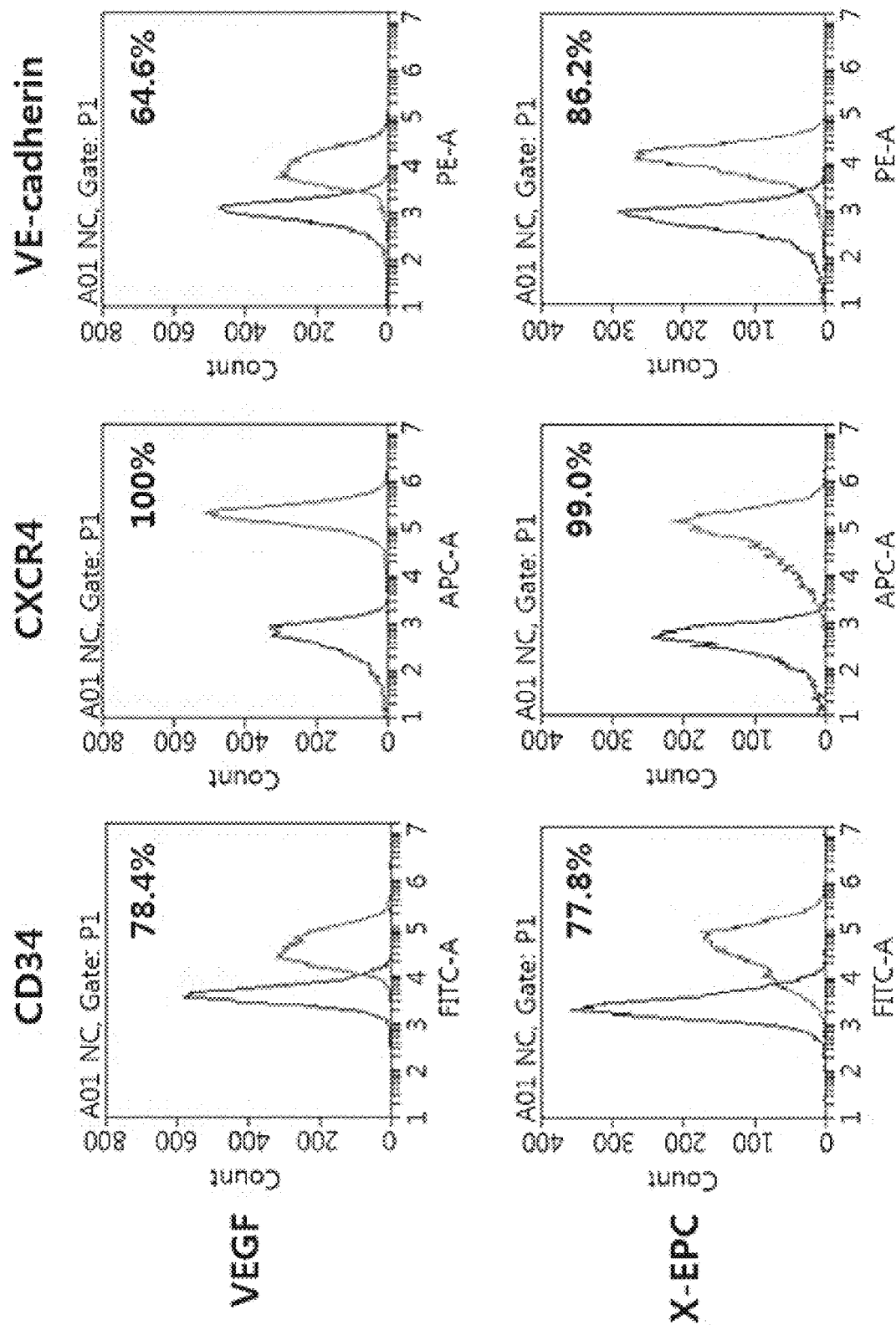
FIG. 14B is a diagram illustrating a result of analyzing the cell cycle changes in vascular stem cells cultured by the xeno-free culture method using mixture 4F according to the present disclosure.

As shown in FIGS. 14A and 14B, it was identified that the cells cultured by the xeno-free culture method using mixture 4F had excellent colony formation ability and had a short division time. However, the control group treated with the single component did not form EPC colonies. However, EPC colonies were identified in the vascular endothelial growth factor-treated cells, but it was identified that the expression of VE-cadherin was low, and the division time of the cells was also prolonged, thereby reducing the proliferative ability of the cells.

Example 15. Stem Cell Differentiation-Related Gene Expression Analysis of Vascular Stem Cells Cultured by the Xeno-Free Culture Method Using Mixture 4F According to the method of Example 11, the expression of stem cell differentiation-related genes in cells cultured in a xeno-free culture method using mixture 4F was analyzed in the same manner as in Example 7. Based on the RNA sequencing results, gene ontology, category, and expression pattern were analyzed. The results of analysis of stem cell differentiation-related gene expression are shown in FIGS. 15 to 17.

Figure 15:
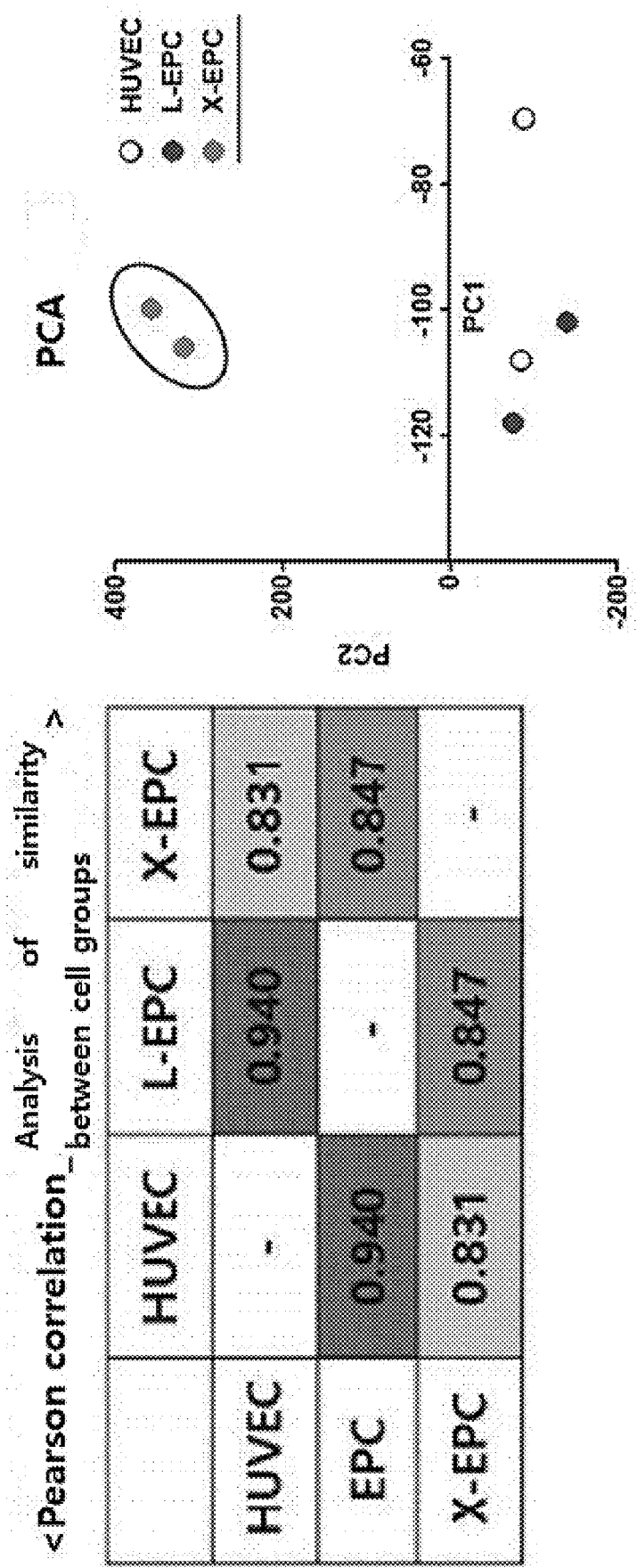
FIG. 15 is a diagram illustrating a result of analyzing the genetic similarity of vascular stem cells and control cells cultured by the xeno-free culture method using mixture 4F according to the present disclosure.

As shown in FIG. 15, cells (X-EPC) cultured by the xeno-free culture method using mixture 4F have genetic differences from L-EPC obtained by the conventional culture method. As a result of PCA analysis of the correlation for each cell group, it was identified that X-EPC had low similarity with each cell group, unlike HUVEC/L-EPC, which showed high similarity.

Figure 16:
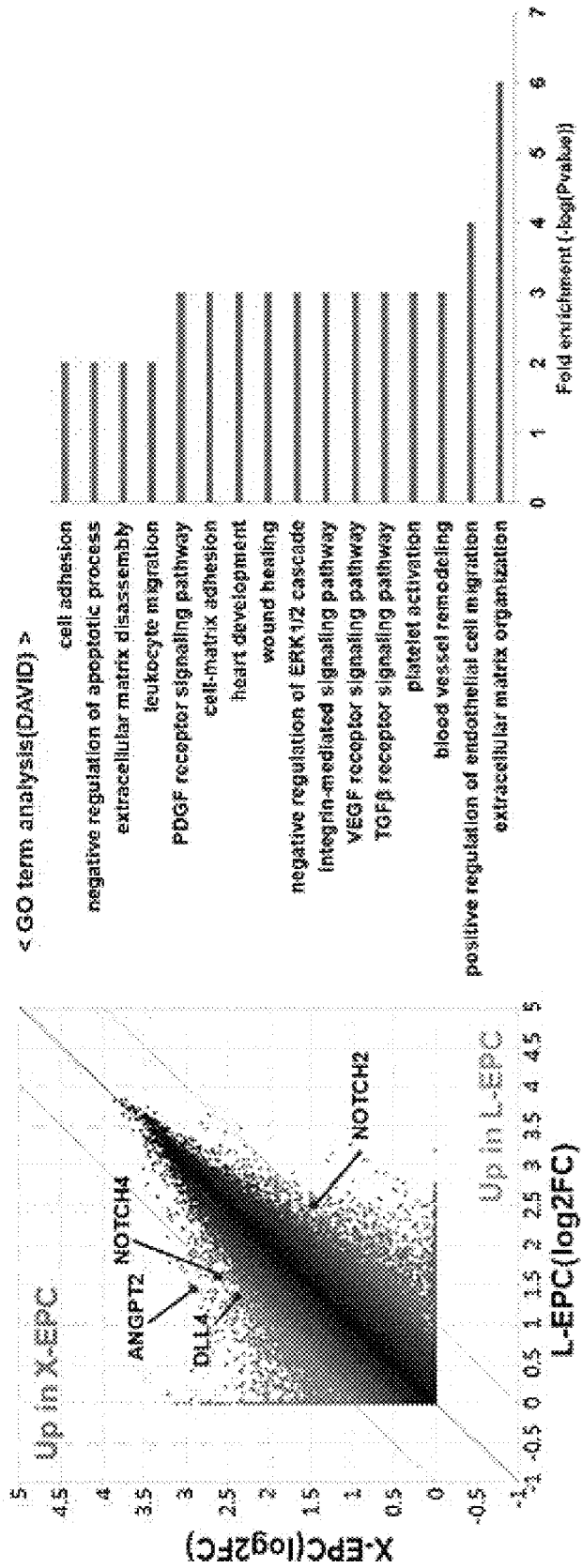
FIG. 16 is a diagram illustrating a result of analyzing the gene ontology and category of vascular stem cells and control cells cultured by the xeno-free culture method using mixture 4F according to the present disclosure.

As shown in FIG. 16, as a result of analyzing gene ontology and categories for genes showing a 2-fold or more difference in expression in X-EPC compared to L-EPC, it was identified that the degree of change in the expression of genes related to endothelial cell activation, angiogenesis, and endothelial cell migration was large.

Figure 17B:
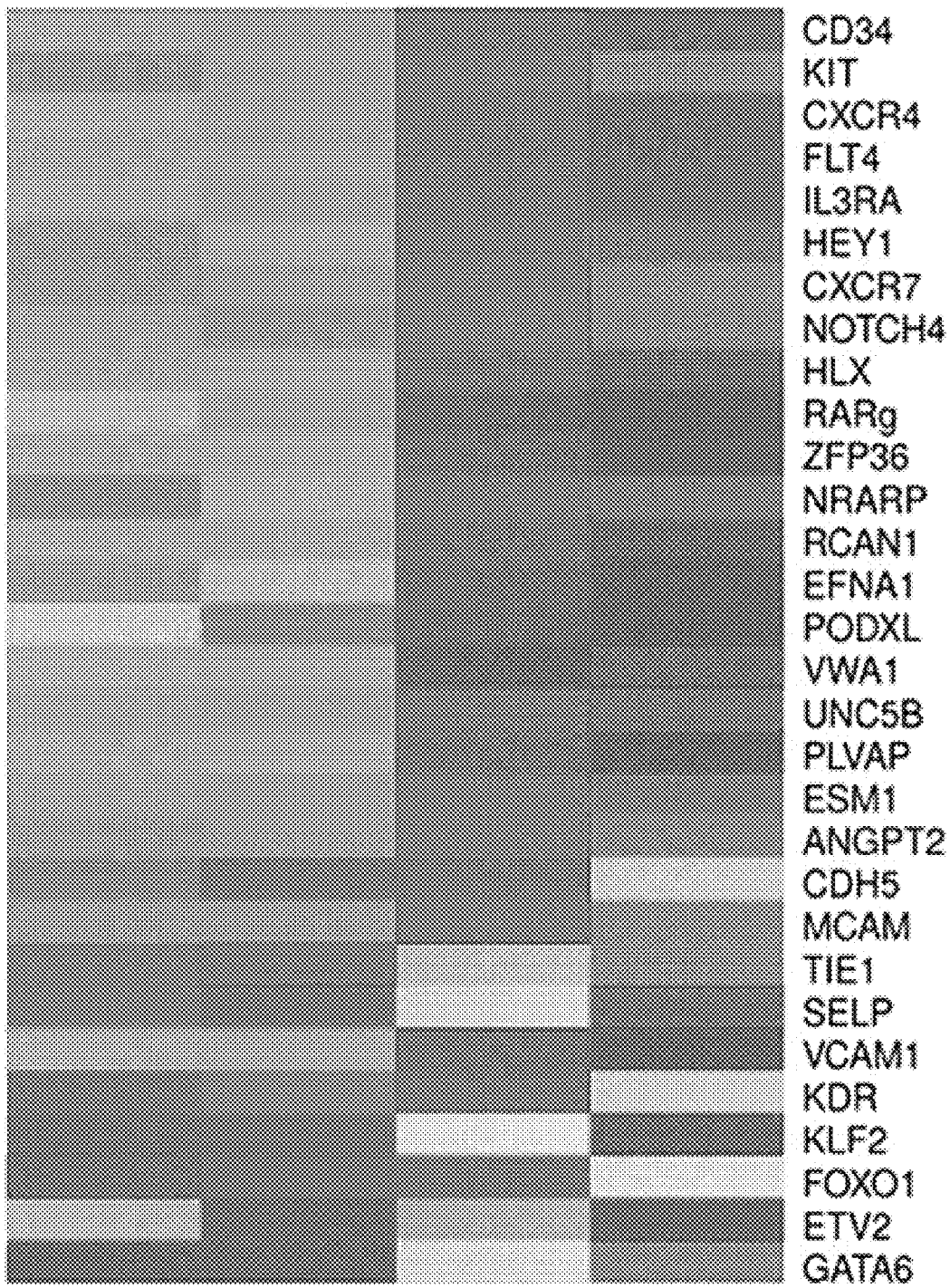
FIG. 17B is a diagram illustrating a change in gene expression level in FIG. 17A as a heat map.

As shown in FIGS. 17A and 17B, it was identified that X-EPC significantly increases the expression of some undifferentiated stem cell-related genes (CD34, KIT, HEY1, PODXL, etc.)

Example 16. Identification of Angiogenic Ability of Vascular Stem Cells Cultured by the Xeno-Free Culture Method Using Mixture 4F According to the method of Example 11, the angiogenic ability of cells cultured by the xeno-free culture method using mixture 4F was identified by the method of Example 10. In addition, in the 3D bead germination assay, each cell was cultured with the beads for culture for 4 hours, and the beads were coated with the cells. Cell-coated culture fibrinogen/thrombin gel was seeded with 100 to 200 cell-coated beads and cultured at 37° C. The degree of angiogenic germination of beads during culture was observed. The analysis results of 2D and 3D angiogenic ability are shown in FIG. 18.

Figure 18:
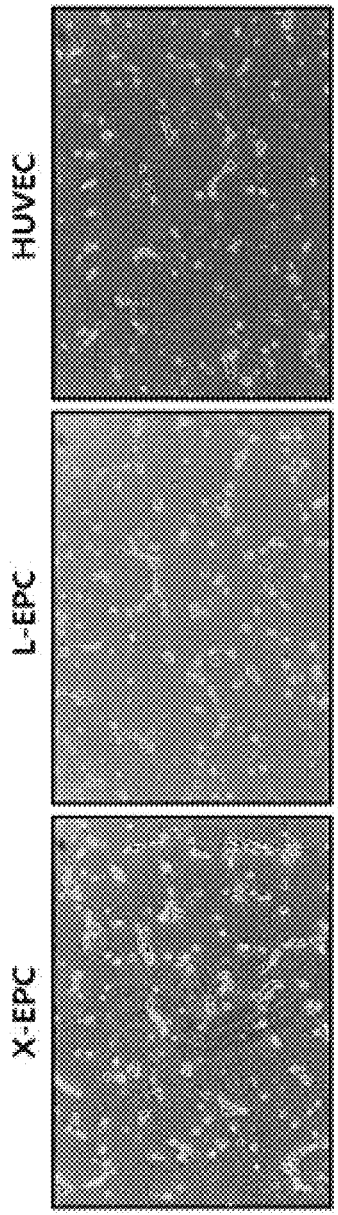
FIG. 18 is a diagram illustrating a result of identifying the angiogenic ability of the vascular stem cells cultured by the xeno-free culture method using mixture 4F according to the present disclosure.
Figure 18:
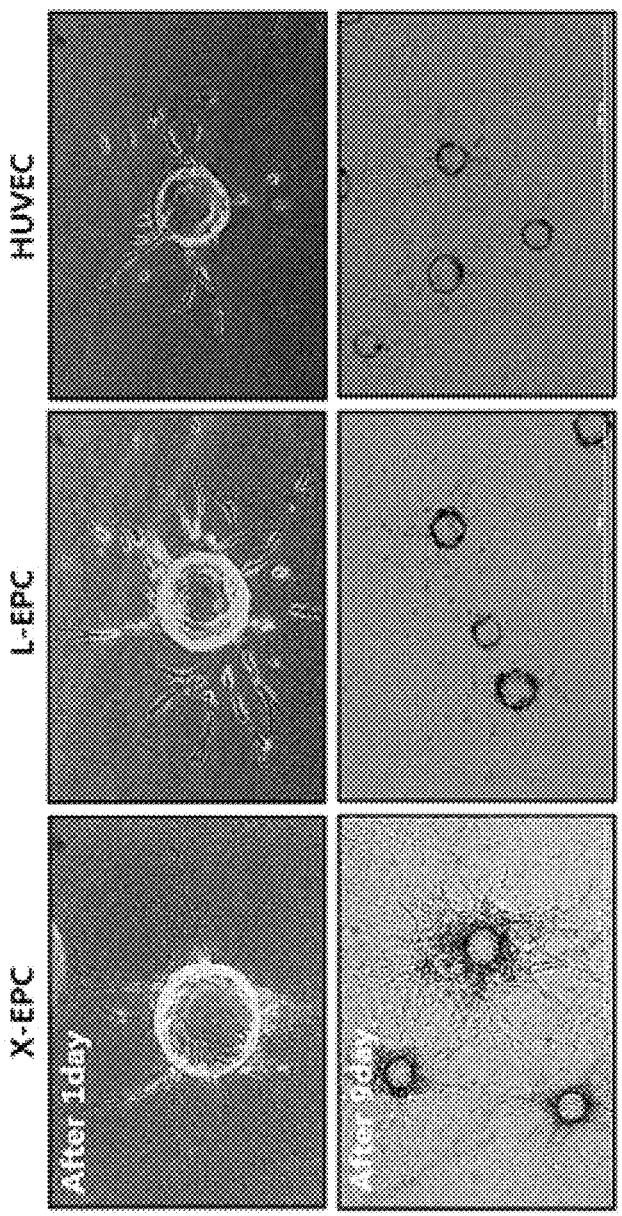

As shown in FIG. 18, it was identified that cells (X-EPC) cultured by the xeno-free culture method using mixture 4F had improved angiogenic ability than L-EPC and HUVEC, and lasted longer.

Example 17. Identification of the Effect of Paracrine Angiogenesis of the Vascular Stem Cells Cultured by the Xeno-Free Culture Method Using Mixture 4F According to the method of Example 11, the effect of paracrine angiogenesis of the cells cultured by the xeno-free culture method using mixture 4F was analyzed. Specifically, total RNA was extracted from the cells of Example 11 using Trizol, and cDNA was synthesized based thereon. In addition, mRNA expression of major angiogenesis-stimulating factors (VEGF-A, IL-8, b-FGF, Ang2) was analyzed by performing qPCR using the synthesized cDNA as a template. The primers used for the PCR are shown in Table 1, and the qPCR results are shown in FIG. 19.

TABLE 1

|         | Forward (5'-3')                                        | Reverse (5'-3')                                       |
|---------|--------------------------------------------------------|-------------------------------------------------------|
| VEGF-A  | GCTCGGTGCT GGAATTTGAT (SEQ ID NO.: 1)                  | GCCCGATTCA AGTGGGGAAT (SEQ ID NO.: 2)                 |
| IL-8    | CACCGGAAGG AACCATCTCA CT (SEQ ID NO.: 3)               | TCAGCCCTCT TCAAAAACTT CTCC (SEQ ID NO.: 4)            |
| b-FGF   | GGAGAAGAGC GACCCTCACA TCAAG (SEQ ID NO.: 5)            | CCAGTTCGTT TCAGTGCCAC ATACCAA (SEQ ID NO.: 6)         |
| Ang2    | GGGAAGGGAA TGAGGCTTAC (SEQ ID NO.: 7)                  | AAGTTGGAAG GACCACATGC (SEQ ID NO.: 8)                 |
| b-actin | AGCGAGCATC CCCCAAAGTT (SEQ ID NO.: 9)                  | GGGCACGAAG GCTCATCATT (SEQ ID NO.: 10)                |

Figure 19:
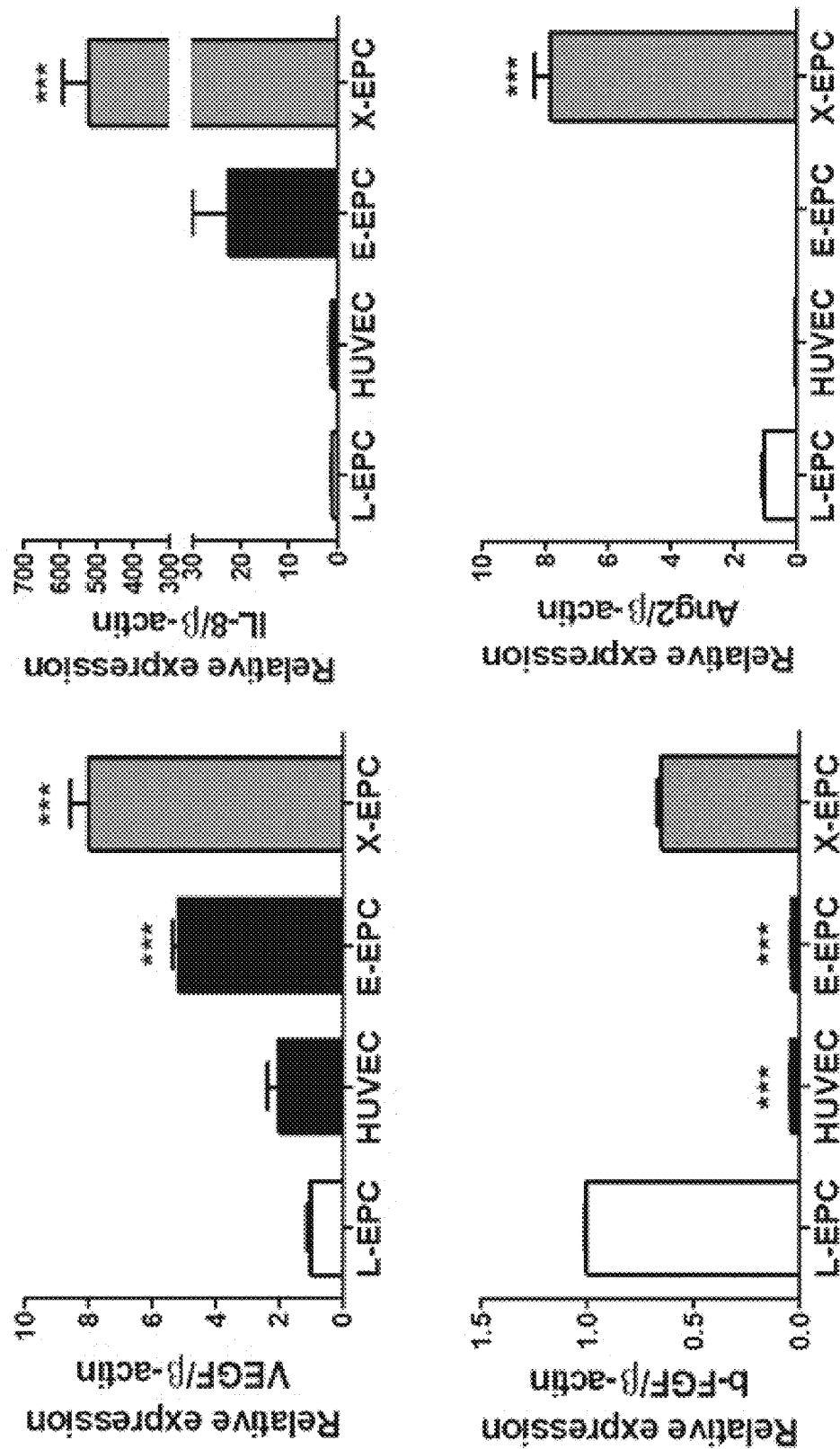
FIG. 19 is a diagram illustrating a result of identifying the effect of paracrine angiogenesis of the vascular stem cells cultured by the xeno-free culture method using mixture 4F according to the present disclosure.

As shown in FIG. 19, it was identified that the expression of major growth factors and cytokines that stimulate angiogenesis in the cells (X-EPC) cultured by the xeno-free culture method using mixture 4F was significantly higher than that of the control group (L-EPC, E-EPC, HUVEC).

Example 18. Identification of the Vascular Regeneration Effect of Vascular Stem Cells Cultured by the Xeno-Free Culture Method Using Mixture 4F in an Animal Model of Lower Extremity Ischemia According to the method of Example 11, the vascular regeneration effect was identified in the cells cultured by the xeno-free culture method using mixture 4F in the same manner as in Example 4, and the results are shown in FIGS. 20 and 21.

Figure 20:
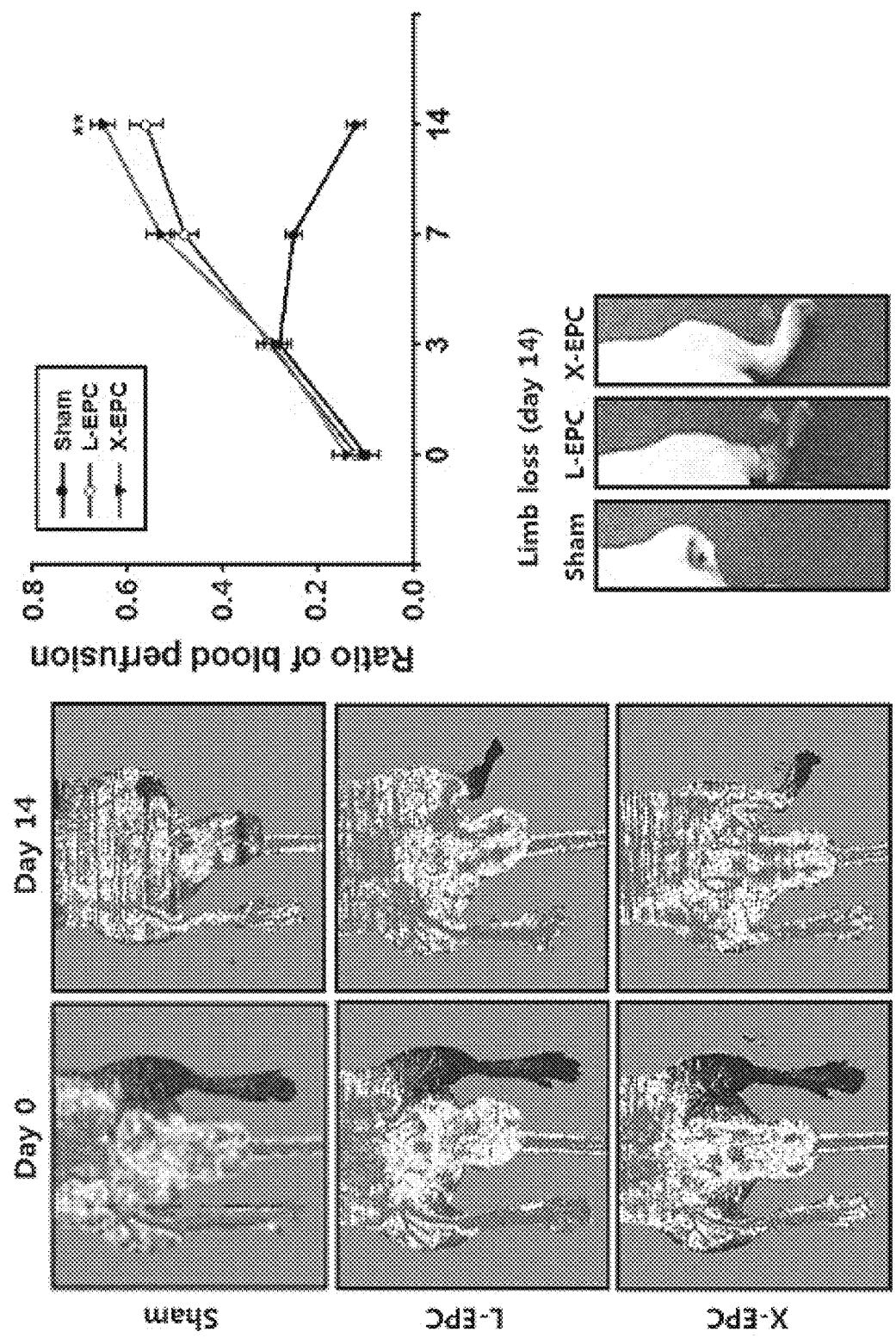
FIG. 20 is a diagram illustrating a result of identifying the vascular regeneration effect in vivo after transplanting the vascular stem cells cultured by the xeno-free culture method using mixture 4F in an animal model of lower extremity ischemia according to the present disclosure.
Figure 21:
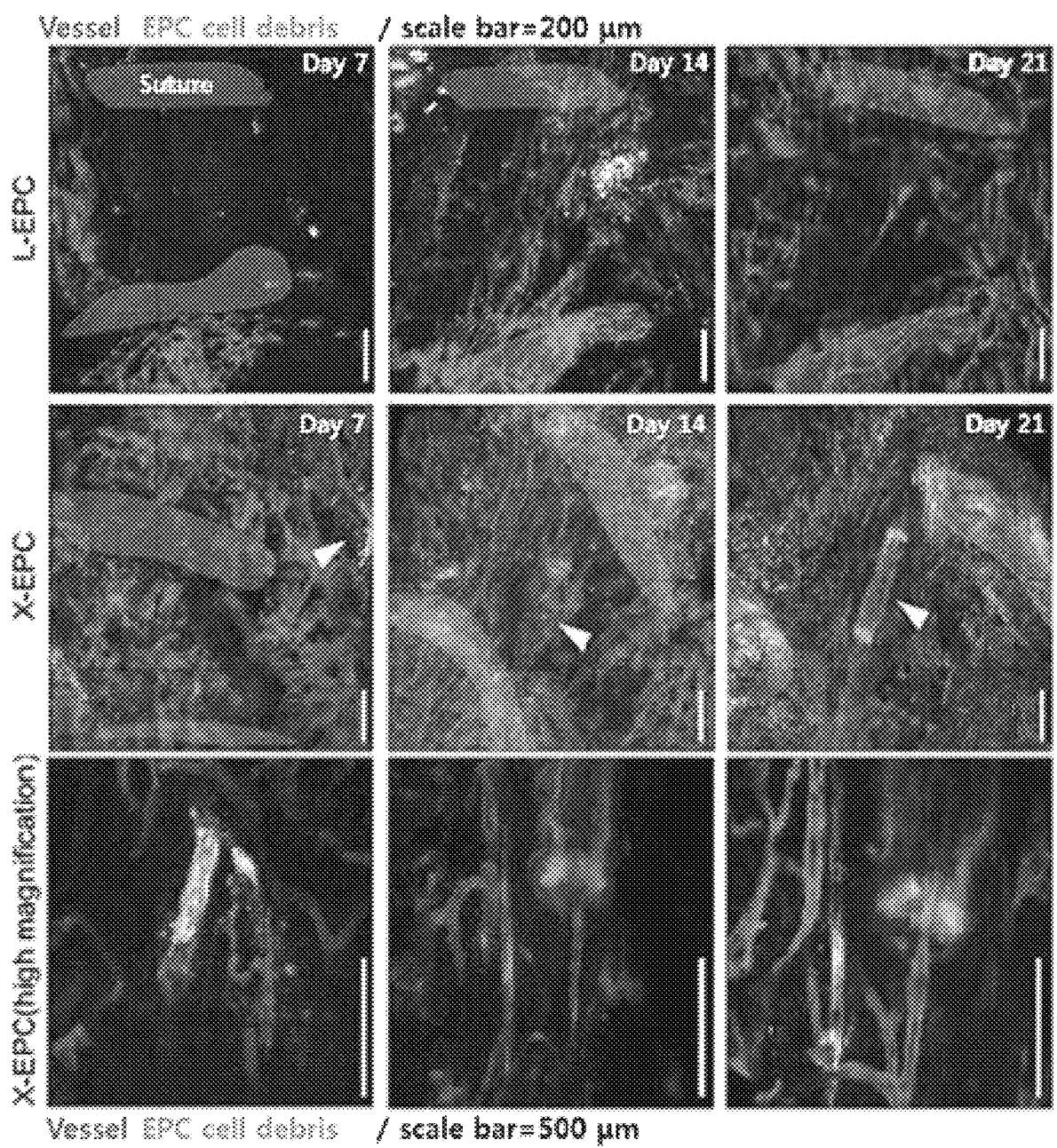
FIG. 21 is a diagram illustrating an image of a vascular suture site after GFP-tagged cells are transplanted using an in vivo imaging technique in an animal model of lower extremity ischemia according to the present disclosure.

As shown in FIGS. 20 and 21, it was identified that in an animal model of lower extremity ischemia, in which cells (X-EPC) cultured by the xeno-free culture method using mixture 4F were transplanted, vascular regeneration in vivo was significantly enhanced compared to that of the control group. In addition, in the animal model of lower extremity ischemia, in which cells (X-EPC) cultured by the xeno-free culture method using mixture 4F were transplanted, a large number of GFP$^+$ cells transplanted around the sutured arterial blood vessels were observed, identifying the phenomenon of entering into existing blood vessels. In the animal model of lower extremity ischemia transplanted with L-EPC, only cell debris was observed 7 days after transplantation, whereas in the animal model of lower extremity ischemia transplanted with X-EPC, the GFP signal of viable cells was detected until day 21 of transplantation. The detection of the GFP signal means that cell engraftment and survival rate are improved. In addition, the animal model of lower extremity ischemia transplanted with X-EPC showed more CD31 (red; mouse vessel) positive blood vessels compared to the group transplanted with L-EPC. The above result means that X-EPC has excellent vascular regeneration effect in vivo.

To sum up, when vascular endothelial progenitor cells are treated with mixture 4F containing fucoidan, a tauroursodeoxycholic acid, oleuropein, and a vascular endothelial growth factor, the vascular endothelial progenitor cells not only acquire undifferentiated characteristics (sternness), but also have the advantage of improving angiogenesis, cell proliferative ability and mobility, thereby improving cell survival and engraftment after transplantation of vascular endothelial progenitor cells into the body and further enhancing the ability to regenerate blood vessels and tissues. Accordingly, the vascular endothelial progenitor cells can have various applications in the fields of stem cell differentiation and ischemic disease prevention and treatment.

Hereinafter, the present disclosure will be described in more detail through formulation examples. The formulation examples are only for illustrating the present disclosure, and the scope of the present disclosure is not to be construed as being limited by the formulation examples.

Formulation Example 1. Preparation of Pharmaceutical Compositions 1-1. Preparation of Powders
  20 mg of mixture 4F
  100 mg of lactose
  10 mg of talc
  The above ingredients are mixed and filled in an airtight bag to prepare powders.
1-2. Preparation of Tablets
  10 mg of mixture 4F
  100 mg of corn Starch
  100 mg of lactose
  2 mg of magnesium stearate After mixing the above ingredients, tablets are prepared by tableting according to a conventional preparation method of tablets.
1-3. Preparation of Capsules
  10 mg of mixture 4F
  3 mg of crystalline cellulose
  14.8 mg of lactose
  0.2 mg of magnesium stearate
  According to a conventional preparation method of capsules, the above ingredients are mixed and filled in a gelatin capsule to prepare capsules.
1-4. Preparation of Injections
  10 mg of mixture 4F
  180 mg of mannitol
  2974 mg of sterile distilled water for injection
  26 mg of $Na_2HPO_4 2H_2O$
  According to a conventional preparation method of injections, the injections are prepared with a content of the above ingredients per 1 ampule (2 ml).
1-5. Preparation of Liquid Formulations
  20 mg of mixture 4F
  10 g of isomerized sugar
  5 g of mannitol
  Appropriate amount of purified water
  According to a conventional preparation method of liquid formulations, each ingredient is added and dissolved in purified water, an appropriate amount of lemon flavor is added. Then, the above ingredients are mixed, purified water is added, the whole is adjusted to a total of 100 ml by adding purified water, and then filled in a brown bottle and sterilized to prepare a liquid formulation.

Hereinabove, a specific part of the present disclosure has been described in detail, for those of ordinary skill in the art, it is clear that this specific description is only a preferred embodiment, and the scope of the present disclosure is not limited thereby.

INDUSTRIAL APPLICABILITY

According to the present disclosure, stem cells treated with mixture 4F not only acquire undifferentiated characteristics (stemness), but also have the advantage of improving cell proliferative ability and mobility, and thus after being transplanted into the body as a therapeutic agent for ischemic diseases, the stem cells can improve cell survival and engraftment, and the ability to regenerate blood vessels and tissues.

Stem cells may be cultured by a xeno-free culture method using mixture 4F The stem cells cultured by the xeno-free culture method acquire higher undifferentiated characteristics, colony formation ability and proliferative ability than cells cultured by the existing culture method, and have high expression of major growth factors and cytokines that stimulate angiogenesis. In addition, the stem cells can improve in vivo cell survival and engraftment and enhance the ability to regenerate blood vessels and tissues.

Therefore, the mixture 4F and the stem cells according to the present disclosure may be usefully used in basic research and clinical fields for the development of therapeutic agents for ischemic diseases.

The invention claimed is:

1. A stem cell culture medium composition containing fucoidan, a tauroursodeoxycholic acid, oleuropein, and a vascular endothelial growth factor,
   wherein the fucoidan is at a concentration of 1 to 300 nM,
   wherein the tauroursodeoxycholic acid is at a concentration of 17.5 to 35 μM,
   wherein the oleuropein is at a concentration of 0.35 to 0.7 μM, and
   wherein the vascular endothelial growth factor is at a concentration of 0.1 to 5 nM.

2. The composition of claim 1, wherein the stem cell is one selected from the group consisting of endothelial progenitor cell, mesenchymal stem cell, embryonic stem cell, myoblast, and cardiac stem cell.

3. The composition of claim 2, wherein the stem cell is endothelial progenitor cell.

4. The composition of claim 1, wherein the composition further comprises human serum.

5. The composition of claim 1, wherein the medium composition is xeno-free medium composition.

6. The composition of claim 1, wherein the medium composition excludes cytokine, growth factor other than the vascular endothelial growth factor and animal serum.

* * * * *